(12) United States Patent
Shigeta et al.

(10) Patent No.: US 9,785,235 B2
(45) Date of Patent: Oct. 10, 2017

(54) DISPLAY CONTROL APPARATUS, DISPLAY CONTROL METHOD OF DISPLAY CONTROL APPARATUS, AND EYE GAZE DIRECTION DETECTION SYSTEM

(71) Applicant: MITSUBISHI ELECTRIC CORPORATION, Tokyo (JP)

(72) Inventors: Asako Shigeta, Tokyo (JP); Takahisa Aoyagi, Tokyo (JP); Tetsuji Haga, Tokyo (JP)

(73) Assignee: Mitsubishi Electric Corporation, Tokyo (JO)

( * ) Notice: Subject to any disclaimer, the term of this patent is extended or adjusted under 35 U.S.C. 154(b) by 0 days.

(21) Appl. No.: 15/114,759

(22) PCT Filed: Feb. 19, 2014

(86) PCT No.: PCT/JP2014/053929
§ 371 (c)(1),
(2) Date: Jul. 27, 2016

(87) PCT Pub. No.: WO2015/125243
PCT Pub. Date: Aug. 27, 2015

(65) Prior Publication Data
US 2016/0342205 A1    Nov. 24, 2016

(51) Int. Cl.
| | | |
|---|---|---|
| G09G 5/00 | (2006.01) | |
| G06F 3/01 | (2006.01) | |
| A61B 3/113 | (2006.01) | |
| A61B 3/00 | (2006.01) | |
| A61B 5/18 | (2006.01) | |
| G06K 9/00 | (2006.01) | |
| G06T 7/70 | (2017.01) | |
| G06F 9/44 | (2006.01) | |

(52) U.S. Cl.
CPC ............ *G06F 3/013* (2013.01); *A61B 3/0041* (2013.01); *A61B 3/113* (2013.01); *A61B 5/18* (2013.01); *G06K 9/00617* (2013.01); *G06T 7/70* (2017.01); *G06F 9/4446* (2013.01); *G06T 2207/30201* (2013.01)

(58) Field of Classification Search
CPC .......... G06F 17/28; G06F 3/013; G06F 3/005; G06F 3/017; G06F 3/0482
USPC ............................................. 345/8, 156, 633
See application file for complete search history.

(56) References Cited

U.S. PATENT DOCUMENTS

5,579,079 A    11/1996    Yamada et al.

FOREIGN PATENT DOCUMENTS

| JP | 6-34874 A | 2/1994 |
|---|---|---|
| JP | 9-238905 A | 9/1997 |
| JP | 2001-204692 A | 7/2001 |
| JP | 2006-044596 A | 2/2006 |
| JP | 3785669 B2 | 6/2006 |
| JP | 2007-136000 A | 6/2007 |
| JP | 2009-015333 A | 1/2009 |
| JP | 2009-183473 A | 8/2009 |
| JP | 2009-232945 A | 10/2009 |

(Continued)

*Primary Examiner* — Calvin C Ma
(74) *Attorney, Agent, or Firm* — Birch, Stewart, Kolasch & Birch, LLP

(57) ABSTRACT

It is determined whether a driver is gazing at a gaze target object in the eye gaze direction, and the eye gaze of the driver is guided by changing a display mode of the gaze target object determined to be gazed at by the driver. Calibration of eye gaze direction detection information is accurately and promptly executed.

18 Claims, 11 Drawing Sheets

(56) References Cited

FOREIGN PATENT DOCUMENTS

| JP | 2012-65781 A | 4/2012 |
|----|--------------|--------|
| JP | 2010-30361 A | 12/2013 |
| JP | 2013-255781 A | 12/2013 |

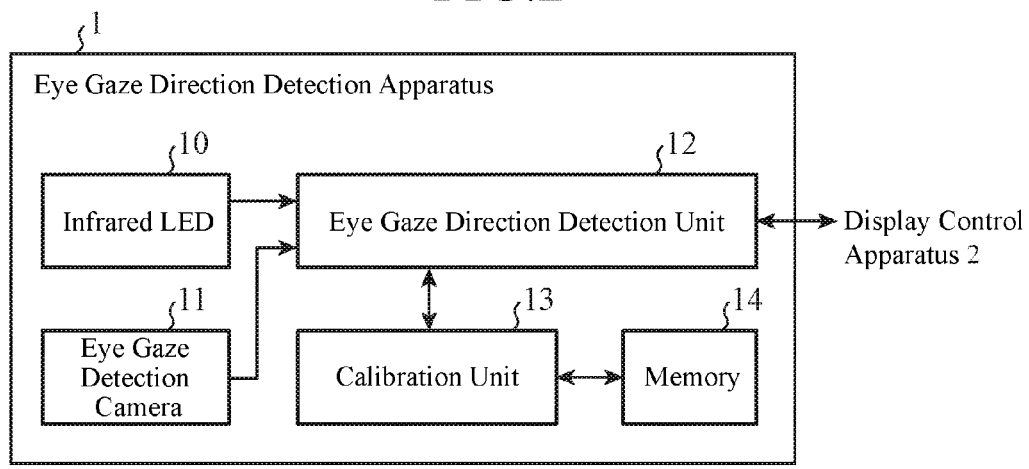
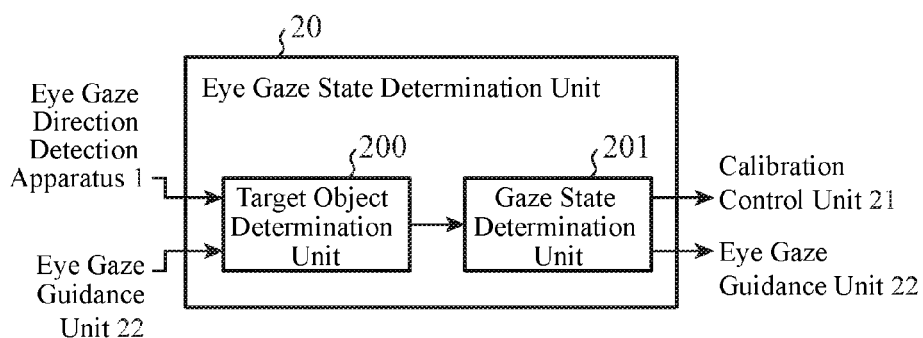
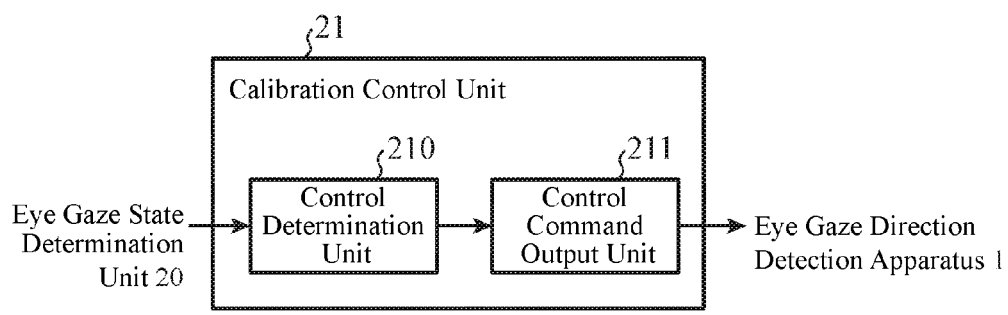

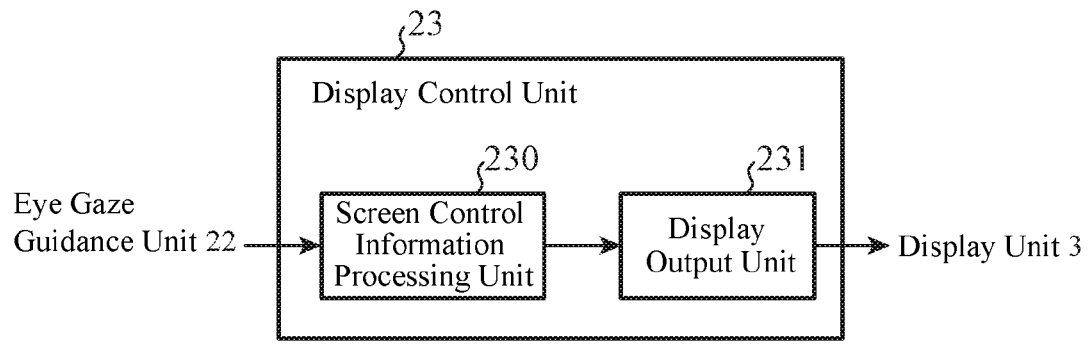
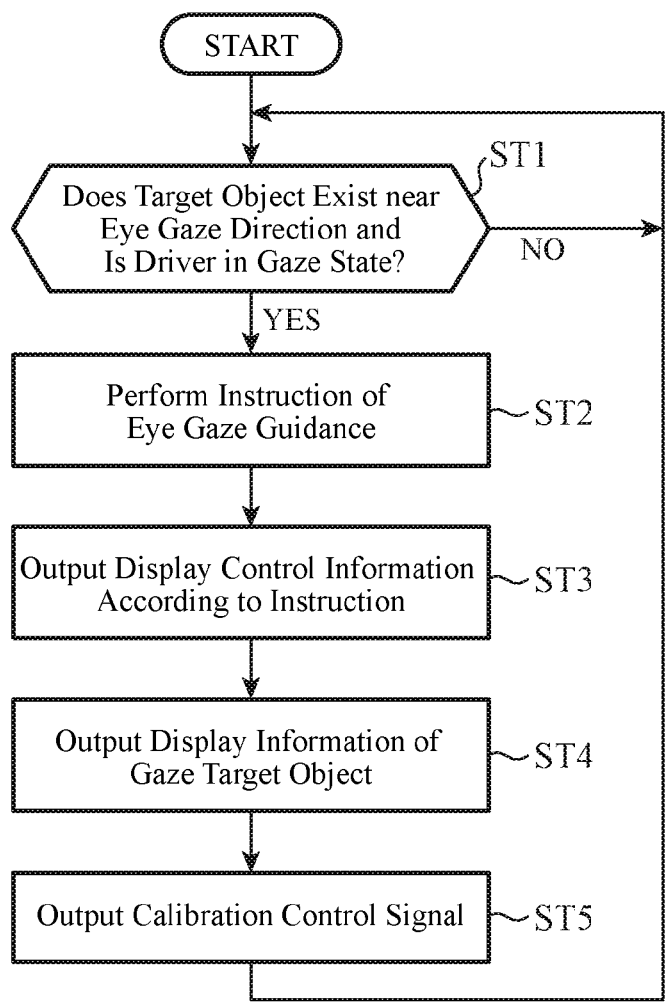

FIG.8
(a)
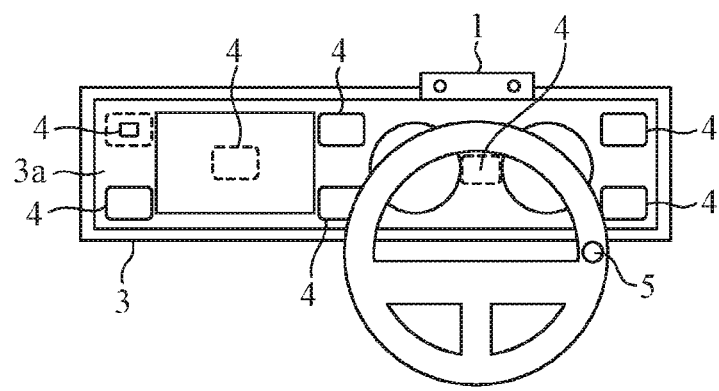
(b)
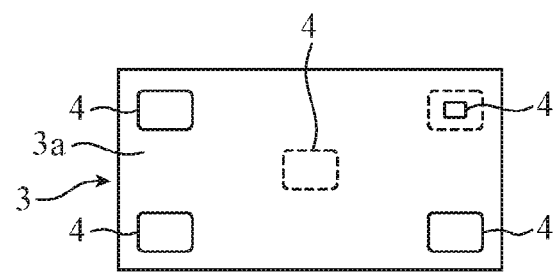
(c)
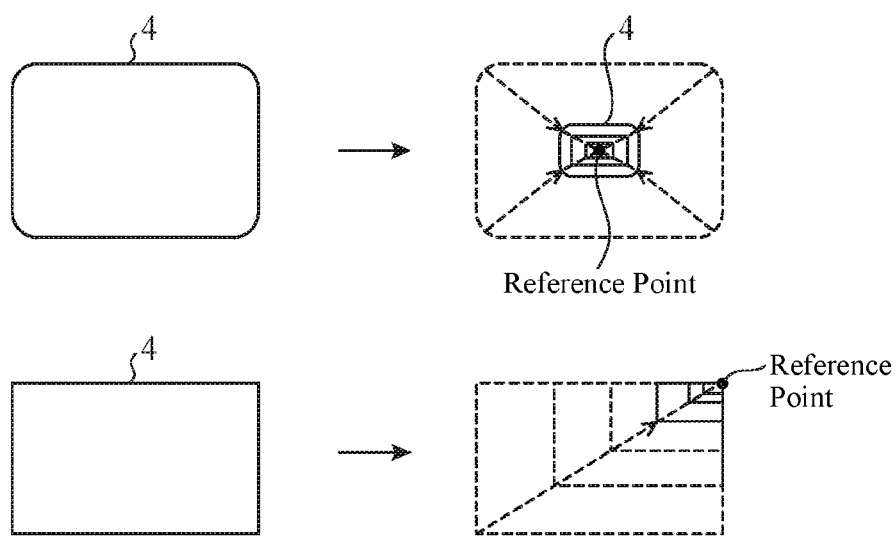
Reference Point
Reference Point

DISPLAY CONTROL APPARATUS, DISPLAY CONTROL METHOD OF DISPLAY CONTROL APPARATUS, AND EYE GAZE DIRECTION DETECTION SYSTEM

TECHNICAL FIELD

The present invention relates to a display control apparatus to control calibration of eye gaze direction detection information that is performed by an eye gaze direction detection apparatus, a display control method of the display control apparatus, an eye gaze direction detection system, and a calibration control method of the eye gaze direction detection system.

BACKGROUND ART

In recent years, there has been proposed systems performing various types of processing using an eye gaze direction of a subject (e.g., driver) that has been detected by an eye gaze direction detection apparatus. For example, there has been proposed many systems that uses the eye gaze direction detection apparatus, such as a detection apparatus for detecting inattentive driving and drowsy driving, and a human-machine interface (HMI) to manipulate an intelligent panel or the like based on an eye gaze.

In addition, there have been proposed various methods of eye gaze direction detection in the eye gaze direction detection apparatus. One of well-known methods is a corneal reflection method. In the corneal reflection method, an eye of a detection subject is irradiated with light of an infrared light-emitting diode (infrared LED), and an eye gaze direction is detected based on a positional relationship between a reflected image on the corneal surface of the eye and the pupil.

The eye gaze direction detection performed by the eye gaze direction detection apparatus generally involves detection errors resulting from individual differences of subjects. It is therefore necessary to ensure detection accuracy by executing so-called calibration for correcting detection error of each subject. In addition, even in a case of an identical subject, if the environment varies with time elapsed from previous calibration, detection error may be generated again. It is therefore desirable to execute calibration periodically.

The calibration performed by an eye gaze direction detection apparatus basically requires the measurement of 2 or more reference points. As the number of measured reference points increases, variations in eye gaze direction detection information are more leveled, and the calibration accuracy improves accordingly. For example, in an apparatus having a quadrangular display unit, it is generally considered desirable to promptly perform calibration of eye gaze direction detection information especially at 4 points near the corner portions and the center point of the display unit which is the intersection of diagonal lines.

However, measurement of a lot of reference points (e.g., 5 points in the above-described example) requires manipulation bothersome for a subject. For example, the subject is required to turn eyes on each of 5 predefined reference points, which puts a burden on the subject. Thus, an apparatus to automatically execute calibration without intention of a subject is demanded. Such an apparatus is proposed in the following documents.

For example, in the apparatuses proposed in Patent Documents 1 and 2, calibration is automatically executed without intention of a driver by using vehicle equipment as a gaze target object serving as a reference point.

Here, examples of the vehicle equipment used as a gaze target object include an inner rear view mirror, a sideview mirror, a navigation system, an air conditioner, a head-up display, and the like.

In Patent Document 1, an eye gaze direction of a driver is detected, and based on the result, vehicle equipment at which the driver is gazing is estimated. Then, the direction of the vehicle equipment viewed from the driver is predefined as a reference of an eye gaze direction, and calibration is executed based on the difference between the reference eye gaze direction and an eye gaze direction detected by an eye gaze direction detection apparatus. In addition, in Patent Document 2, calibration of an eye gaze direction detection apparatus is executed by associating an eye gaze obtained when a driver is manipulating each device, with the position of a corresponding manipulated device. In addition, Patent Document 2 also discloses a case of estimating, based on the distribution state of gaze points of the driver, that the gaze target object exists at the center of the distribution state.

CITATION LIST

Patent Documents

Patent Document 1: JP 2010-30361 A
Patent Document 2: JP 1997-238905 A (JP H09-238905 A)

SUMMARY OF INVENTION

Problems to be Solved by the Invention

In Patent Documents 1 and 2, vehicle equipment viewable from a driver is used as a gaze target object for the purpose of completing calibration without making the driver be aware.

However, it is unknown when the vehicle equipment is viewed by the driver. It may therefore take a long time until 2 or more reference points are measured.

Thus, in the related arts disclosed in Patent Documents 1 and 2, proper calibration cannot be performed promptly. As a result, a state in which eye gaze direction detection information includes detection error may continue for a long time. During this time period, there is no guarantee that a system using the above-described eye gaze direction detection apparatus can be accurately manipulated.

In addition, in Patent Documents 1 and 2, since vehicle equipment is used as a gaze target object, the size of the gaze target object is larger than that of a gaze target object commonly used for calibration. For this reason, the driver is unlikely to intensively gaze at, for example, a predefined reference point, and there is a problem that the variation becomes large in eye gaze direction detection information obtained by the eye gaze direction detection apparatus. Thus, even if a same vehicle equipment is viewed, the variation in the eye gaze direction is large, so that it is difficult to improve calibration accuracy.

Furthermore, when an inner rear view mirror and a sideview mirror are used as gaze target objects as in Patent Document 2, an obstacle is not always reflected in the central part of the inner rear view mirror or the sideview mirror. Thus, for example, even if an eye gaze direction serving as a reference point is set at the central part of the inner rear view mirror, the driver does not always view the central part of the inner rear view mirror, and as a result, deviation occurs.

For this reason, even in the case of detecting an eye gaze direction using the distribution state of gaze points collected when a driver is viewing an obstacle through a mirror, there is a high possibility that detection results are biased.

Furthermore, if calibration is performed based on the distribution state of gaze points at which the driver has gazed, the driver needs to gaze at the inner rear view mirror or the sideview mirror many times, which takes time.

Furthermore, when a manipulation switch of an in-vehicle device is used as a gaze target object, the driver does not always manipulate the manipulation switch with viewing the center point of the manipulation switch. In this case, if the manipulation switch is made smaller, the variation in eye gaze direction detection information is expected to become smaller. However, if the manipulation switch is made smaller, there is concern that the visibility of the manipulation switch or the operability of the device using this manipulation switch deteriorates.

The present invention has been devised for solving the above-described problems, and an object of the present invention is to obtain a calibration control apparatus and a calibration control method that can accurately and appropriately perform calibration for eye gaze direction detection of a subject, and an eye gaze direction detection system using the same.

The present invention has been devised for solving the above-described problems, and an object of the present invention is to obtain a display control apparatus, a display control method of the display control apparatus, an eye gaze direction detection system, and a calibration control method of the eye gaze direction detection system that can accurately and promptly perform calibration of eye gaze direction detection information of a subject.

Means for Solving the Problems

A display control apparatus according to the present invention uses a display object displayed by a display unit as a gaze target object, and controls calibration of an eye gaze direction detection apparatus based on the gaze target object. The display control apparatus includes an eye gaze state determinator to determine, based on eye gaze direction detection information detected by the eye gaze direction detection apparatus and display information of the display object, whether a subject is gazing at the gaze target object existing in an eye gaze direction of the subject, an eye gaze guider to output display information of the gaze target object and screen control information relating to a display mode of the gaze target object, and to guide an eye gaze of the subject by changing the display mode of the gaze target object when the subject is determined to be gazing at the gaze target object, a display controller to output display control information for controlling the display unit, based on the screen control information output by the eye gaze guider, and a calibration controller to output a calibration control signal toward the eye gaze direction detection apparatus when the subject is determined to be gazing at the gaze target object.

Effects of Invention

According to the present invention, there is an effect of enabling accurate and prompt calibration of eye gaze direction detection information of a subject.

BRIEF DESCRIPTION OF DRAWINGS

FIG. 2 is a block diagram illustrating a configuration of an eye gaze direction detection apparatus in FIG. 1;

FIG. 3 is a block diagram illustrating a configuration of an eye gaze state determination unit in FIG. 1;

FIG. 4 is a block diagram illustrating a configuration of a calibration control unit in FIG. 1;

FIG. 6 is a block diagram illustrating a configuration of a display control unit in FIG. 1;

FIG. 7 is a flowchart illustrating an operation of a display control apparatus according to a first embodiment of the present invention;

FIGS. 8(a) to 8(c) are diagrams each of which illustrates an example of a display screen for performing eye gaze guidance by scaling down a gaze target object toward a reference point;

MODES FOR CARRYING OUT THE INVENTION

For describing the present invention in more detail, some embodiments for carrying out the present invention will be described below in accordance with the attached drawings.

First Embodiment

Figure 1:
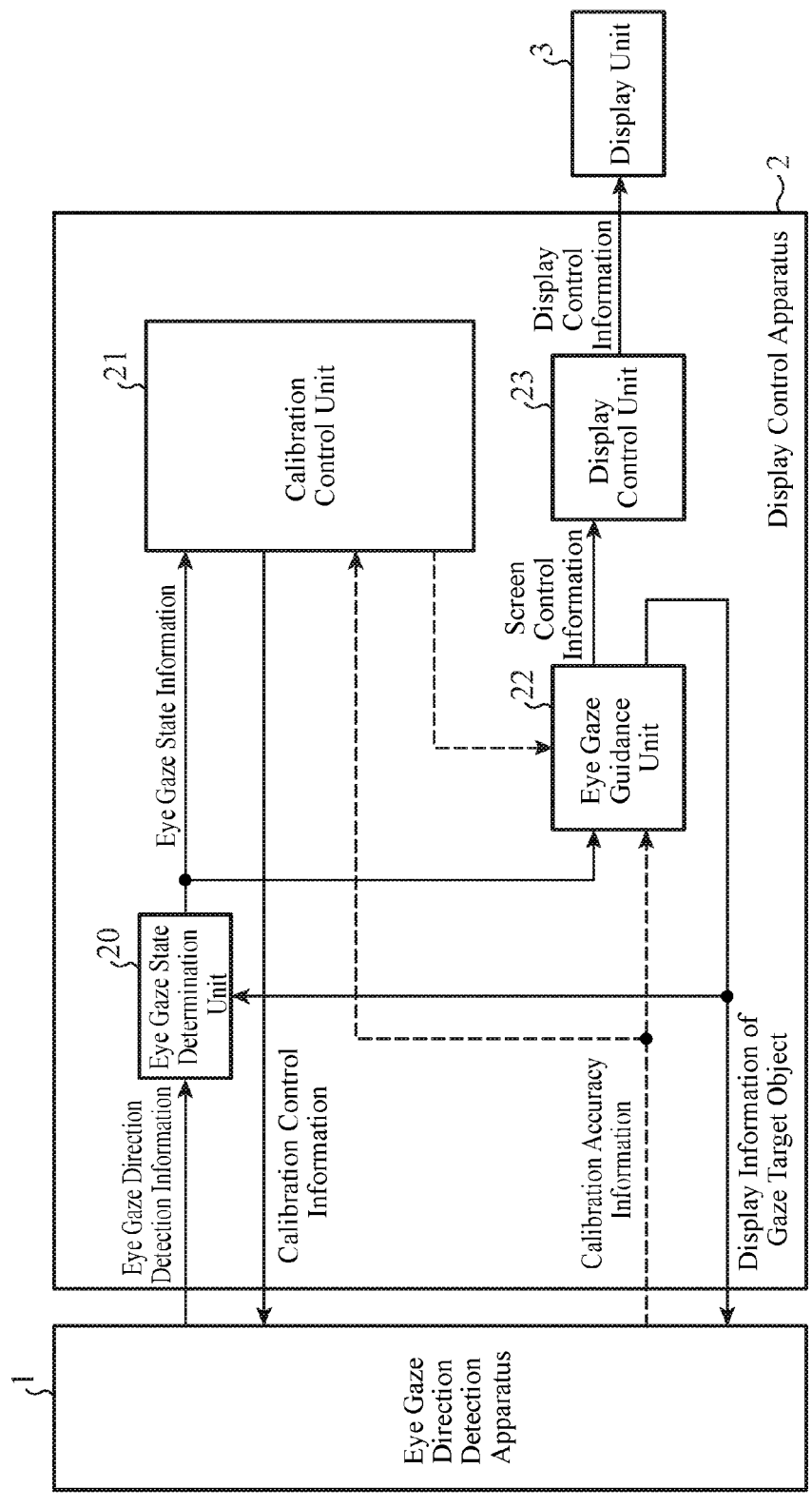
FIG. 1 is a block diagram illustrating a configuration of an eye gaze direction detection system according to a first embodiment of the present invention.

FIG. 1 is a block diagram illustrating a configuration of an eye gaze direction detection system according to a first embodiment of the present invention. The eye gaze direction detection system illustrated in FIG. 1 is a system mounted on a movable body such as a vehicle, which detects an eye gaze direction of a driver serving as a subject, and includes an eye gaze direction detection apparatus 1, a display control apparatus 2, and a display unit 3.

The eye gaze direction detection apparatus 1 is installed in front of the driver within a vehicle cabin and outputs eye gaze direction detection information including an eye gaze direction of the driver. The eye gaze direction detection information of the subject that has been detected by the eye gaze direction detection apparatus 1 is used in, for example, a detection apparatus for detecting inattentive driving and drowsy driving, and an HMI to manipulate an intelligent panel or the like based on an eye gaze.

The display control apparatus 2 uses a display object displayed by the display unit 3 as a gaze target object, and controls calibration of eye gaze direction detection information output by the eye gaze direction detection apparatus 1 based on this gaze target object, and includes an eye gaze state determination unit 20, a calibration control unit 21, an eye gaze guidance unit 22, and a display control unit 23.

The gaze target object is a predefined display object displayed by the display unit 3, and used as a reference point to be gazed at by the driver. Examples of the gaze target object include an icon and a button displayed by an intelligent panel functioning as a display unit, or by a display unit of a car navigation apparatus, and a marking displayed by a head-up display (hereinafter, abbreviated as "HUD") functioning as a display unit. In addition, the reference point is voluntarily defined in accordance with the display unit, and is set at a position desirable for executing calibration of eye gaze direction detection information. In addition, the case of 5 reference points has been described above as an example of reference points. However, the number of reference points to be set may be smaller than 5, or in contrast, may be larger than 5, according to the display unit to be applied.

The display unit 3 changes screen display in accordance with the display control information obtained from the display control apparatus 2, and is installed in front of the driver within the vehicle cabin, for example.

In addition, the display unit 3 may be a display device to display vehicle information, navigation information, audio information, air conditioner information, etc., like an intelligent panel. In addition, the display unit 3 may be a car navigation system, a display audio, an HUD, or the like.

Note that, the flows of information indicated by the broken lines in FIG. 1 are merely required in embodiments to be described later, and are not always required. Thus, the flows of information indicated by the broken lines will be described in respective parts in which explanation thereof are required, and the descriptions thereof are omitted here.

In FIG. 1, the eye gaze direction detection apparatus 1 detects an eye gaze direction of the driver, and supplies the eye gaze direction detection information to the eye gaze state determination unit 20. The eye gaze state determination unit 20 obtains the eye gaze direction detection information, and display information of a gaze target object that is to be obtained from the eye gaze guidance unit 22, which will be described later. Based on these pieces of information, the eye gaze state determination unit 20 determines whether a gaze target object such as the above-described icon or the like exists in the eye gaze direction of the driver. When a gaze target object exists, the eye gaze state determination unit 20 further determines whether the driver is gazing at the gaze target object. The eye gaze state determination unit 20 outputs eye gaze state information as a result of these determinations. The eye gaze state information is given to the calibration control unit 21 and the eye gaze guidance unit 22.

The eye gaze guidance unit 22 guides the eye gaze of the driver based on the eye gaze state information. For example, when the driver is determined to be gazing at a specific icon as a gaze target object, by scaling down the display range of this icon toward a reference point, the eye gaze guidance unit 22 guides the eye gaze of the driver toward the reference point. In other words, by scaling down the display range of this icon toward the reference point, the eye gaze guidance unit 22 guides the eye gaze of the driver toward the reference point without driver's awareness. This is implemented in the following manner. When the driver is determined to be gazing at a specific icon, the eye gaze guidance unit 22 supplies screen control information to the display control unit 23 so as to scale down the display range of this icon toward the reference point, thereby performing eye gaze guidance. Upon receiving the screen control information, the display control unit 23 generates display control information based on the screen control information, and scales down the icon toward the reference point on the display unit 3.

The eye gaze guidance unit 22 further outputs display information of the gaze target object. The display information includes a position of an icon serving as a gaze target object, i.e., position information of a reference point, and the like.

The display information of the gaze target object is given to the eye gaze direction detection apparatus 1 and the eye gaze state determination unit 20. In other words, the eye gaze direction detection apparatus 1 outputs eye gaze direction detection information, and obtains display information of a gaze target object. At this time, if the position of the gaze target object can be identified, the eye gaze direction detection apparatus 1 can calculate the eye gaze direction of the driver. Thus, the eye gaze direction detection apparatus 1 becomes capable of calibrating the eye gaze direction detection information based on the eye gaze direction detection information and the eye gaze direction of the driver that has been obtained through the above-described calculation.

Meanwhile, the execution timing of calibration and the like are set according to a calibration control signal to be given by the calibration control unit 21 to the eye gaze direction detection apparatus 1. Specifically, for example, when the driver is gazing at a specific icon, and a predetermined time has elapsed, it is determined that the state is stable based on the eye gaze state information output from the eye gaze state determination unit 20, and then, an execution instruction of calibration of eye gaze direction detection information is issued at the time using the calibration control signal.

Note that, the above-described operation of each unit has been briefly described as an example, and the details thereof will be described below. In addition, broken line parts will be described later as required.

FIG. 2 is a block diagram illustrating a configuration of the eye gaze direction detection apparatus 1 in FIG. 1. As illustrated in FIG. 2, the eye gaze direction detection apparatus 1 includes an infrared LED (Light-Emitting Diode) 10, an eye gaze detection camera 11, an eye gaze direction detection unit 12, a calibration unit 13, and a memory 14.

The infrared LED 10 is an LED to emit infrared light of various patterns onto eyes of the driver. For example, the infrared LED 10 emits near-infrared light to which human eyes are less sensitive. In addition, the eye gaze detection camera 11 acquires an image of the face or eyes of the driver that is irradiated by the infrared LED 10 with infrared light. For the eye gaze detection camera 11, a CCD, that can capture infrared light or the like, is used.

The eye gaze direction detection unit 12 performs image analysis of image data captured by the eye gaze detection camera 11 to detect and output eye gaze direction detection information indicating the eye gaze direction. As a detection method of the eye gaze direction detection information, a corneal reflection method that uses infrared light is commonly known. However, other methods may be used. Further, only the eye gaze detection camera 11 may be used without the use of the infrared LED 10, and the eye gaze direction may be detected through image analysis from the captured image data.

The calibration unit 13 has a function of performing calibration processing of eye gaze direction detection information obtained by the eye gaze direction detection unit 12. More specifically, the calibration unit 13 executes calibration of eye gaze direction detection information based on the eye gaze direction detection information obtained by the eye gaze direction detection unit 12 and display information of the gaze target object existing in the eye gaze direction. The execution timing of calibration is set according to calibration control information from the calibration control unit 21.

For example, the calibration unit 13 obtains eye gaze direction detection information detected by the eye gaze direction detection unit 12. In addition, the calibration unit 13 obtains, from the display control apparatus 2, display information of the gaze target object existing in the eye gaze direction detected by the eye gaze direction detection unit 12. Examples of the display information of the gaze target object include data on the position, size information, moving state, and the like of a corresponding icon or the like. Using these pieces of information, calibration data for eye gaze direction detection information is calculated. The calibration data calculated by the calibration unit 13 is set in the eye gaze direction detection unit 12. In addition, using the calibration data, the eye gaze direction detection unit 12 corrects calculation processing of detecting the eye gaze direction. Calibrated eye gaze direction detection information can be thereby calculated.

The memory 14 is a storage unit to store information to be used for calculation of calibration data. For example, the calibration unit 13 stores eye gaze direction detection information obtained when the driver gazes at a predetermined gaze target object in the memory 14. In addition, as display information of the gaze target object which is detected by the eye gaze direction detection unit 12, the calibration unit 13 stores data on the display range, the position of a reference point, the moving state and the like of the gaze target object. These pieces of information are accumulated in the memory 14 as information obtained when an identical gaze target object has been viewed. Then, in the calibration unit 13 and the like, predetermined processing such as calculating an average value or a moving average is performed on the accumulated information pieces. Then, calibration data probable for the gaze target object is calculated and is used.

Further, as described above, all pieces of information accumulated and stored in the memory 14 may be subjected to processing such as averaging for calculating calibration data. Alternatively, by calculating normal distribution or the like, part of information having reliability of a predetermined level or more may be extracted for using in the calculation.

FIG. 3 is a block diagram illustrating a configuration of the eye gaze state determination unit 20 in FIG. 1. The eye gaze state determination unit 20 determines whether the driver is gazing at a gaze target object in the eye gaze direction based on the eye gaze direction detection information detected by the eye gaze direction detection apparatus 1 and the display information of the gaze target object from the eye gaze guidance unit 22. As a configuration for implementing the above-described operation, as illustrated in FIG. 3, the eye gaze state determination unit 20 includes a target object determination unit 200 and a gaze state determination unit 201.

The target object determination unit 200 determines whether a gaze target object exists in the eye gaze direction of the driver, based on the eye gaze direction detection information detected by the eye gaze direction detection apparatus 1 and the display information of the gaze target object from the eye gaze guidance unit 22.

For example, the target object determination unit 200 determines whether an icon or the like that serves as a predefined gaze target object exists in a display region that falls within a predetermined range from the eye gaze direction of the driver on the display unit 3. Here, the phrase "within the predetermined range" is used to indicate the range within a circle having the radius of, for example, about 4 to 5 cm that is drawn on the display unit 3 around the center point located on the eye gaze direction detected by the eye gaze direction detection apparatus 1.

In addition, at the stage where calibration has never been performed, an offset error of the eye gaze direction is large. It is therefore considered that, even if the driver gazes at a gaze target object, the gaze target object is not included in a display region that falls within the above-described predetermined range from the eye gaze direction of the driver. In this case, the target object determination unit 200 may determine that the driver gazed at the gaze target object closest to the eye gaze direction. In addition, also when a plurality of gaze target objects exists within the range of a circle having the radius of 4 to 5 cm that is drawn on the display unit 3 around the center point located on the eye gaze direction of the driver, the display object displayed at a position closest to the eye gaze direction of the driver is used as the gaze target object.

The gaze state determination unit 201 determines a driver's state of gazing at a gaze target object, based on eye gaze direction detection information detected by the eye gaze direction detection apparatus 1.

For example, in a state in which eye gaze direction detection information detected by the eye gaze direction detection apparatus 1 includes less variation, it is determined that the driver is gazing at the gaze target object. On the other hand, in a state in which the eye gaze direction detection information of the driver varies significantly, it is determined that the driver is not gazing at the gaze target object, and the eye gaze is moving. Here, the determination that the driver is gazing at a gaze target object is performed based on the fact that the eye gaze direction detection information falls within a range of the same area as that of the display range of the gaze target object, for example. Alternatively, even when the eye gaze direction detection information falls outside the range of the area, if the average of the eye gaze direction detection information is located within the range of the area, it may be determined that the driver is gazing at the gaze target object.

In addition, the gaze state determination unit 201 outputs eye gaze state information to the calibration control unit 21 and the eye gaze guidance unit 22. Here, the eye gaze state information includes information indicating whether a gaze target object exists in the eye gaze direction of the driver, and information regarding the gaze state that indicates whether the driver is gazing at the gaze target object.

FIG. 4 is a block diagram illustrating a configuration of the calibration control unit 21 in FIG. 1. The calibration control unit 21 generates and outputs calibration control information for controlling calibration processing of eye gaze direction detection information of the driver that is obtained by the eye gaze direction detection apparatus 1. As a configuration for implementing the above-described operation, as illustrated in FIG. 4, the calibration control unit 21 includes a control determination unit 210 and a control command output unit 211.

The control determination unit 210 determines control matters of the calibration processing based on the eye gaze state information given by the eye gaze state determination unit 20, i.e., the existence or absence of a gaze target object, and the gaze state. In addition, based on this determination, the control determination unit 210 outputs appropriate calibration control information to the control command output unit 211.

For example, when it is detected that a gaze target object exists in the eye gaze direction of the driver, and that the driver is gazing at the gaze target object, the control determination unit 210 determines to start calibration of eye gaze direction detection information for the eye gaze direction detection apparatus 1.

In response to this determination, the control command output unit 211 outputs calibration control information indicating that calibration is to be started, to the eye gaze direction detection apparatus 1. Specifically, the control command output unit 211 gives a calibration data save start command to the eye gaze direction detection unit 12 of the eye gaze direction detection apparatus 1.

At this time, the eye gaze guidance unit 22 illustrated in FIG. 1 outputs display information of the gaze target object that includes position information of the gaze target object at which the driver is gazing, when the control command output unit 211 outputs the calibration data save start command to the eye gaze direction detection apparatus 1. As a result, the eye gaze direction detection unit 12 obtains the detected eye gaze direction of the driver and the position of the gaze target object (the true value of the eye gaze direction of the driver).

In addition, as described later, control commands output by the control command output unit 211 include control commands such as, for example, a calibration data save start command, a calibration data save stop command, a calibration data calculation command, and a calibration data update command.

Figure 5:
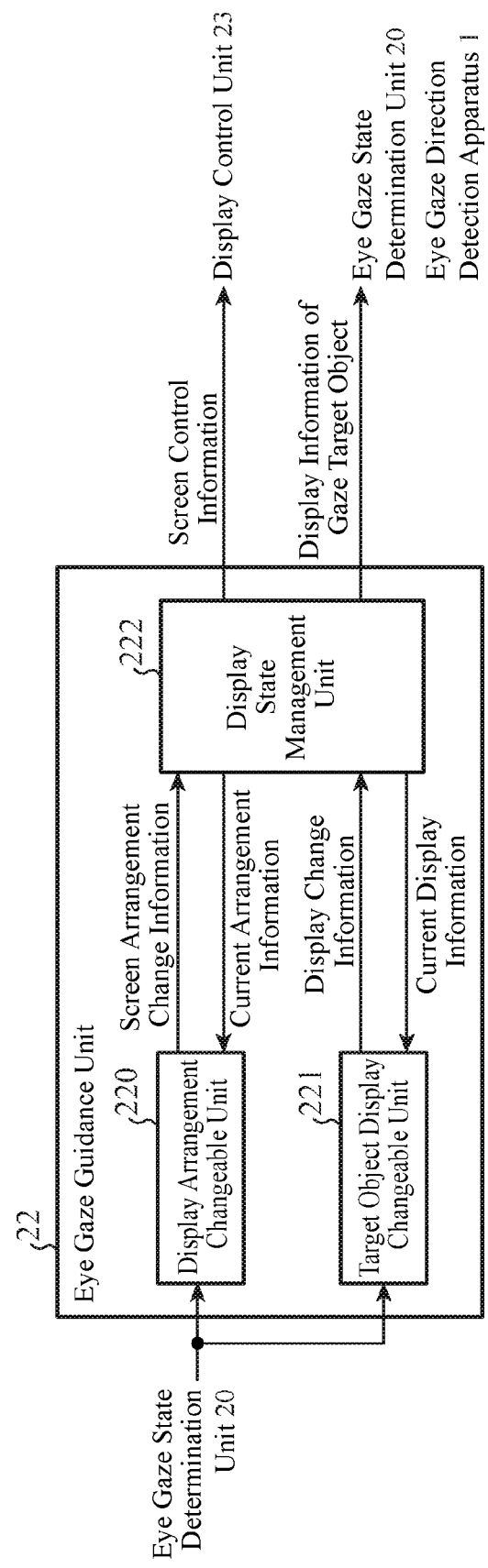
FIG. 5 is a block diagram illustrating a configuration of an eye gaze guidance unit in FIG. 1.

FIG. 5 is a block diagram illustrating a configuration of the eye gaze guidance unit 22 in FIG. 1. The eye gaze guidance unit 22 performs eye gaze guidance of a driver using a gaze target object determined to be gazed at by the driver by the eye gaze state determination unit 20. As a configuration for implementing the above-described operation, as illustrated in FIG. 5, the eye gaze guidance unit 22 includes a display arrangement changeable unit 220 and a target object display changeable unit 221.

The display arrangement changeable unit 220 changes the display arrangement of a gaze target object based on eye gaze state information input from the eye gaze state determination unit 20 and current arrangement information obtained from a display state management unit 222.

For example, when the driver is determined to be gazing at a first gaze target object, the display arrangement changeable unit 220 generates screen arrangement change information for arranging a second gaze target object to be gazed at subsequently to the first gaze target object at a position different from the position of the first gaze target object, and output the generated screen arrangement change information to the display state management unit 222.

In an example case, the first gaze target object is a selection key of manipulation items, and the second gaze target object corresponds to the determination key to determine a manipulation item selected using the selection key. At this time, the display arrangement changeable unit 220 arranges the determination key, serving as the second gaze target object, on the diagonal of the display unit 3 with respect to the selection key serving as the first gaze target object. Namely, the display arrangement changeable unit 220 takes in the arrangement information of the selection key, serving as the first gaze target object, as current arrangement information from the display state management unit 222. Based on this information, the display arrangement changeable unit 220 outputs, to the display state management unit 222, screen arrangement change information for instructing that the determination key serving as the second gaze target object is to be arranged on the diagonal of the display unit 3. Based on the above-described screen arrangement change information from the display arrangement changeable unit, the display state management unit 222 outputs screen control information toward the display control unit 23. At the same time, the display state management unit 222 outputs display information of the gaze target object to the eye gaze state determination unit 20 and the eye gaze direction detection apparatus 1. In this manner, the eye gaze guidance unit 22 guides the eye gaze of the driver to move on the diagonal after the driver gazes at the selection key to reach the determination key. With this configuration, at each of 2 points being diagonal positions of the display unit 3, calibration of eye gaze direction detection information can be executed.

Note that, the selection key serving as the first gaze target object and the determination key serving as the second gaze target object do not have to be drawn at the same time. For example, in the transition from a first screen displaying a selection key being the first gaze target object to a second screen displaying a determination key being the second gaze target object, the arrangement in which the position of the selection key on the first screen and the position of the determination key on the second screen becomes diagonal to each other may be adopted.

The target object display changeable unit 221 changes a display mode of a gaze target object based on eye gaze state information input from the eye gaze state determination unit 20 and current display information obtained from the display state management unit 222. The target object display changeable unit 221 generates display change information indicating the change of a display mode such as, for example, the reduction ratio at which the gaze target object is scaled down, and the position of a reference point that is set in scaling down, and a moving angle (moving direction) and a moving speed at which the gaze target object is moved on a screen, and outputs the generated display change information to the display state management unit 222.

Here, for example, when the driver is determined to be gazing at a gaze target object, by scaling down the gaze target object toward a reference point, the eye gaze of the driver is guided so that the driver gazes at the reference point. As a result, the eye gaze of the driver is guided to the reference point whichever part of the gaze target object the driver is viewing. Thus, by executing calibration assuming that the true eye gaze direction of the driver is the reference point, calibration of eye gaze direction detection information can be accurately executed.

Further, by moving a gaze target object determined to be gazed at by the driver toward a predefined direction, the eye gaze of the driver is guided so as to follow the movement of the gaze target object. As a result, by comparing the angle information indicating the movement of the eye gaze detected by the eye gaze direction detection apparatus 1 with the true angle information obtained from the movement information of the actually moved gaze target object, calibration can be executed for the angle by which the eye gaze has changed.

In addition, the display state management unit 222 receives the above-described screen arrangement change information or display change information, and generates screen control information based on these pieces of information to supply the generated screen control information to the display control unit 23. At the same time, the display state management unit 222 outputs display information of the gaze target object toward the eye gaze state determination unit 20 and the eye gaze direction detection apparatus 1.

FIG. 6 is a block diagram illustrating a configuration of the display control unit 23 in FIG. 1. The display control unit 23 controls the display of the display unit 3. In addition, the display control unit 23 guides the eye gaze of a driver on the display unit 3 by generating display control information in accordance with the screen control information input from the eye gaze guidance unit 22 and supplying the generated display control information to the display unit 3. As a configuration for implementing the above-described operation, as illustrated in FIG. 6, the display control unit 23 includes a screen control information processing unit 230 and a display output unit 231.

Based on the screen control information input from the eye gaze guidance unit 22, the screen control information processing unit 230 generates display information so as to perform display in accordance with the screen control information, and outputs the generated display information to the display output unit 231.

Based on the display information input from the screen control information processing unit 230, the display output unit 231 generates display control information and outputs the generated display control information to the display unit 3. As a result, based on the display information generated by the screen control information processing unit 230, the display unit 3 performs display to guide the eye gaze of the driver.

Each of the eye gaze state determination unit 20, the calibration control unit 21, the eye gaze guidance unit 22, and the display control unit 23 can be implemented as a specific means in which hardware and software cooperate with each other, by a microcomputer executing a program in which processing specific to the first embodiment is described, for example. Note that, the above-described program can be described in the read only memory (ROM) electrically connected to the microcomputer, for example. In addition, the RAM (random access memory) electrically connected to the microcomputer can be used as a storage device for temporarily storing results of various calculations executed by the microcomputer.

Next, an operation will be described.

FIG. 7 is a flowchart illustrating an operation of the display control apparatus 2 according to the first embodiment of the present invention. FIG. 7 illustrates an example of performing calibration of eye gaze direction detection information of a driver that is detected by the eye gaze direction detection apparatus 1 illustrated in FIG. 1. Here, the operation of the flowchart in FIG. 7 is assumed to start upon key-on.

In addition, when power is applied to each configuration of the eye gaze direction detection system illustrated in FIG. 1, required initialization processing is assumed to be executed as preprocessing in each of the eye gaze direction detection apparatus 1, the display control apparatus 2, and the display unit 3. In the initialization, the calibration unit 13 of the eye gaze direction detection apparatus 1 may read calibration data already registered in the memory 14, and set the read calibration data in the eye gaze direction detection unit 12.

Upon completion of the initialization processing, the eye gaze direction detection apparatus 1 starts eye gaze direction detection of the driver, and sequentially outputs the obtained eye gaze direction detection information to the display control apparatus 2.

Based on the eye gaze direction detection information input from the eye gaze direction detection apparatus 1 and display information of a gaze target object that is given by the eye gaze guidance unit 22, the eye gaze state determination unit 20 of the display control apparatus 2 determines whether a gaze target object exists in a display region of the display unit 3 that is located near the eye gaze direction of the driver, and the driver is in the gaze state of gazing at the gaze target object (step ST1).

Specifically, based on the eye gaze direction detection information detected by the eye gaze direction detection apparatus 1 and the display information of a gaze target object that has been input from the eye gaze guidance unit 22, the target object determination unit 200 of the eye gaze state determination unit 20 determines whether a gaze target object being gazed at by the driver exists among gaze target objects currently displayed by the display unit 3.

For example, as described above, when a gaze target object exists in a range of a circle having the radius of 4 to 5 cm that is drawn on the display unit 3 around the eye gaze direction of the driver, it is determined that the gaze target object exists in the display region of the display unit 3 that is located near the eye gaze direction of the driver. However, in a case where calibration of the eye gaze direction detection apparatus 1 has never been performed, the display object displayed at a position closest to the eye gaze direction of the driver is used as the gaze target object. In addition, also when a plurality of gaze target objects exists within a range of a circle having the radius of 4 to 5 cm that is drawn on the display unit 3 around the eye gaze direction of the driver, the display object displayed at a position closest to the eye gaze direction of the driver is used as the gaze target object.

For example, when the variation in eye gaze direction detection information of the driver remains within a predetermined range (e.g., within a range having an area substantially equivalent to the display area of the gaze target object) until a predetermined time (e.g., 0.5 seconds) elapses, it is determined that the driver is gazing at the gaze target object. Alternatively, when an average value of movement amounts of the eye gaze in a predetermined time is within a range having that area, it is determined that the driver is gazing at the gaze target object.

When a gaze target object does not exist near the eye gaze direction of the driver, or the driver is obviously not gazing at the gaze target object near the eye gaze direction (step ST1; NO), the processing returns to the processing in step ST1, and the above-described determination is repeated.

On the other hand, when a gaze target object exists near the eye gaze direction of the driver, and the driver is gazing at the gaze target object (step ST1; YES), the eye gaze state determination unit 20 outputs, to the eye gaze guidance unit 22, information about the existence or absence of a gaze target object at which the driver is gazing (if such a gaze target object exists, an identification number of the gaze target object is output as the information) and the gaze state thereof.

Based on the gaze target object determined to be gazed at by the driver, the eye gaze guidance unit 22 generates screen control information for instructing the eye gaze guidance of the driver, and outputs the generated screen control information to the display control unit 23 (step ST2). Then, according to the screen control information input from the eye gaze guidance unit 22, the display control unit 23 outputs a display control signal toward the display unit 3 so as to cause the display unit 3 to perform display for guiding the eye gaze of the driver (step ST3).

In the following, each of the operation of the target object display changeable unit 221 and the operation of the display arrangement changeable unit 220 will be described.

First, the target object display changeable unit 221 of the eye gaze guidance unit 22 generates instruction information for changing a display mode of a gaze target object based on the gaze state of the gaze target object.

For example, based on the eye gaze state information obtained from the eye gaze state determination unit 20, a gaze target object determined to be gazed at by the driver is identified from the identification number of the gaze target object. Then, the target object display changeable unit 221 has a function of generating, when it is detected that the gaze target object is not scaled down based on the current display information of the identified gaze target object, display change information for performing display so as to scale down the gaze target object toward a predefined reference point. Alternatively, the target object display changeable unit 221 has a function of generating display change information for moving a gaze target object on the display unit 3 based on the current display information of the identified gaze target object. Based on these pieces of display change information, the display state management unit 222 generates screen control information and outputs the generated screen control information to the display control unit 23. Here, the screen control information regarding the identified gaze target object is, for example, information on the reduction ratio at which the gaze target object is scaled down, the position of a reference point that is set in scaling down, the speed of scaling down, or the like, or information indicating the moving angle (moving direction) and the moving speed at which the gaze target object is moved on the screen. Based on the screen control information input from the eye gaze guidance unit 22, the screen control information processing unit 230 of the display control unit 23 generates display information for causing the display unit 3 to perform display in accordance with the screen control information, and outputs the generated display information to the display output unit 231. Upon receiving the display information, the display output unit 231 generates display control information and outputs the generated display control information to the display unit 3. Then, the display mode of the gaze target object in the display unit 3 is changed to a display mode for guiding the eye gaze of the driver. The details of the display will be described later using FIGS. 8, 10, and 11.

In addition, based on the identification number and the gaze state of the gaze target object determined to be gazed at by the driver, the display arrangement changeable unit 220 of the eye gaze guidance unit 22 changes the arrangement on the display unit 3 of a gaze target object to be gazed at subsequently to the gaze target object determined to be gazed at.

For example, when the gaze target object is determined from the identification number of the gaze target object to be a display object of a predefined type, for example, a selection key relating to a manipulation item of selecting a function, the gaze target object is used as the first gaze target object. In addition, the determination key for determining a manipulation item that is to be gazed at subsequently to the selection key is used as the second gaze target object. In this case, the display arrangement changeable unit 220 has a function of obtaining current display information from the display state management unit 222, generating screen arrangement change information for arranging the second gaze target object at a position different from the position of the first gaze target object, based on the obtained current display information, and outputting the generated screen arrangement change information to the display state management unit 222. The display state management unit 222 generates screen control information based on the screen arrangement change information, and outputs the generated screen control information to the display control unit 23.

Based on the screen control information input from the eye gaze guidance unit 22, the screen control information processing unit 230 of the display control unit 23 generates display information for causing the display unit 3 to perform display in accordance with the screen control information, and outputs the generated display information to the display output unit 231. Upon receiving the display information, the display output unit 231 generates display control information and outputs the generated display control information to the display unit 3. The details of the display will be described later using FIGS. 9 and 12.

The eye gaze guidance unit 22 outputs display information of the gaze target object including the position of the gaze target object, to the eye gaze state determination unit 20, and also outputs the display information toward the eye gaze direction detection apparatus 1 (step ST4). The eye gaze direction detection apparatus 1 thereby obtains eye gaze direction detection information and display information of the gaze target object which indicates the true eye gaze direction. Thus, by comparing both of them, the eye gaze direction detection apparatus 1 can execute calculation of calibration so as to match the eye gaze direction detection information with the true eye gaze direction.

The calibration control unit 21 outputs a calibration control signal toward the eye gaze direction detection apparatus 1 (step ST5). For example, after it has been determined that the driver is gazing at a gaze target object (step ST1), and the display unit 3 performs display for eye gaze guidance (step ST2, step ST3), the calibration control unit 21 outputs a calibration data save start command for instructing the eye gaze direction detection apparatus 1 to start measuring calibration data, and to save the measured calibration data. Here, the calibration data refers to information required for executing calibration of eye gaze direction detection information, and refers to, for example, information relating to a difference between the eye gaze direction detection information and the true eye gaze direction of the driver.

The eye gaze direction detection apparatus 1 thereby measures calibration data at a frequency of, for example, 30 times per 1 second (30 Hz), and saves the measured calibration data into the memory 14. Note that, a sufficient number of samples to be stored in the memory 14 is about 30 in each reference point. Namely, after the eye gaze is determined to be stabilized in 0.5 seconds, which is a condition of determining that the driver is gazing at, the calibration at the reference point may be ended in about 1 second. Thus, it is enough for the calibration control unit 21 to output a calibration data save stop command after a predetermined time (e.g., 1 to 2 seconds) from when the calibration control unit 21 output the above-described calibration data save start command. In response to the calibration data save stop command, saving of the calibration data into the memory 14 is stopped.

If samples of calibration data are collected, the calibration unit 13 can calculate reliable calibration data. Thus, after outputting the calibration data save stop command, the calibration control unit 21 outputs a calibration data calculation command to the eye gaze direction detection apparatus 1. Based on the calibration data calculation command, the calibration unit 13 calculates calibration data. Then, the obtained calibration data is transmitted to the memory 14, and storage or information update is performed. Thus, subsequently to the calibration data calculation command, the calibration control unit 21 outputs a calibration data update command to the eye gaze direction detection apparatus 1 (step ST5).

As described above, control commands in step ST5 include a calibration data save start command, a calibration data save stop command, a calibration data calculation command, a calibration data update command, and the like.

In addition, in the above description, the calibration data save stop command is output after the predetermined time of 1 to 2 seconds after the output of the calibration data save start command. Nevertheless, when it is determined that the driver stops gazing at the gaze target object before the lapse of the predetermined time, a calibration data save stop command is promptly output. This is because, in a state in which the driver is not gazing at a gaze target object, calibration of eye gaze direction detection information for the gaze target object cannot be executed.

Alternatively, the following processing may be adopted: the calibration data save start command is output in response to pressing of a predetermined switch by the driver; and the calibration data save stop command is output in response to pressing of the switch again. This is because, since calibration is executed based on the intention of the driver, the driver is considered to be gazing at a gaze target object during the period.

Furthermore, in the case of an apparatus in which, after the driver has gazed at a manipulation key, the manipulation item is determined by pressing a determination key for determining this manipulation item, the following processing may be adopted: the calibration data save start command is output when the eye gaze of the driver has moved from the gaze at the manipulation key and it is determined that the driver is gazing at the determination key; and the calibration data save stop command is output when the driver presses the determination key. This is because, when the driver presses the determination key, it is estimated that the predetermined time of about 1 to 2 seconds has sufficiently elapsed since the driver was determined to be gazing at the determination key until the determination key is pressed.

The eye gaze direction detection unit 12 corrects calculation processing of detecting an eye gaze direction, using the calibration data obtained through the above-described processing. Calibrated eye gaze direction detection can be thereby executed for each driver.

In addition, even in a case of an identical driver, if environment varies with time elapsed from the execution of calibration, a detection error may be generated again. Thus, it is desirable to execute calibration processing periodically or at the timing in accordance with each predetermined trigger (e.g., when the driver getting in the vehicle, or the like). In this first embodiment, the flowchart in FIG. 7 is executed triggered by key-on. Thus, calibration of eye gaze direction detection information is executed every time key-on is performed. Note that, the execution trigger of calibration is not limited to key-on, and various modes can be conceived by the one skilled in the art.

Next, eye gaze guidance processing will be described using a specific example.

FIG. 8 is a diagram illustrating an example of a display screen for performing eye gaze guidance by scaling down a gaze target object. FIG. 8(*a*) illustrates a case in which the display unit 3 is an instrument panel display arranged on an instrument panel (hereinafter, abbreviated as "IP") provided in front of the driver's seat. In addition, FIG. 8(*b*) illustrates a case in which the display unit 3 is an HUD for projection-displaying information on a windshield provided in front of the driver's seat, a projection plate provided between the steering wheel and the windshield, or the like. The eye gaze direction detection apparatus 1 is provided at a position near the display unit 3 facing the driver, and emits light of an infrared light-emitting diode to the driver.

In the present embodiment, as illustrated in FIGS. 8(*a*) and 8(*c*), a display object to be displayed by the display unit 3 on a display screen 3*a* is used as a gaze target object 4 to be gazed at by the driver. For example, a predefined icon image, button image, marking, or the like is used as the gaze target object 4, and the identification number for identifying each of these display objects is set in the eye gaze guidance unit 22.

Note that, as the gaze target object 4, any display object displayed on the display unit 3 may be used as a gaze target object, or a predefined display object may be used as a gaze target object. In addition, as indicated by a broken line in FIG. 8(*a*) or 8(*b*), the gaze target object 4 may be set at the central part of the display unit 3.

When the eye gaze state determination unit 20 determines that the driver is gazing at a certain gaze target object 4 among gaze target objects 4 displayed on the display screen 3*a*, the target object display changeable unit 221 of the eye gaze guidance unit 22 generates display change information for scaling down this gaze target object 4 gazed by the driver toward a reference point. The display change information is information on the reduction ratio of scaling down the gaze target object 4, the position of the reference point that is set in scaling down, the speed of scaling down, or the like.

Based on the display change information and current display information, the display state management unit 222 generates screen control information and outputs the generated screen control information to the display control unit 23. Upon receiving the screen control information, the display control unit 23 generates display control information and outputs the generated display control information toward the display unit 3. As a result, in the case of the IP display illustrated in FIG. 8(*a*), a top-left gaze target object 4 is displayed in such a manner as to be gradually scaled down toward the center thereof. Similarly, in the case of the HUD illustrated in FIG. 8(*b*), a top-right gaze target object 4 is displayed in such a manner as to be gradually scaled down toward the center thereof. Here, as the scaling-down display of the gaze target object 4, those illustrated in FIG. 8(*c*) can be considered. As one of the scaling-down display, the center of the gaze target object 4 is set as the reference point, and the gaze target object 4 is displayed while being gradually scaled down toward the reference point. Alternatively, when the gaze target object has a rectangular shape, any 1 point of 4 corners of the rectangle is set as the reference point, and the gaze target object 4 is displayed while being gradually scaled down toward the reference point. Namely, as the scaling-down of the gaze target object, the gaze target object does not necessarily have to be scaled down toward the center of the gaze target object. In this manner, the driver gazed at the gaze target object, and subsequently, the eye gaze of the driver is guided toward the reference point, through the display change in which the display size of the gaze target object is scaled down.

Consequently, the driver becomes to gaze at the reference point of the gaze target object 4, so that calibration accuracy of eye gaze direction detection information in the reference point is improved.

Figure 9:
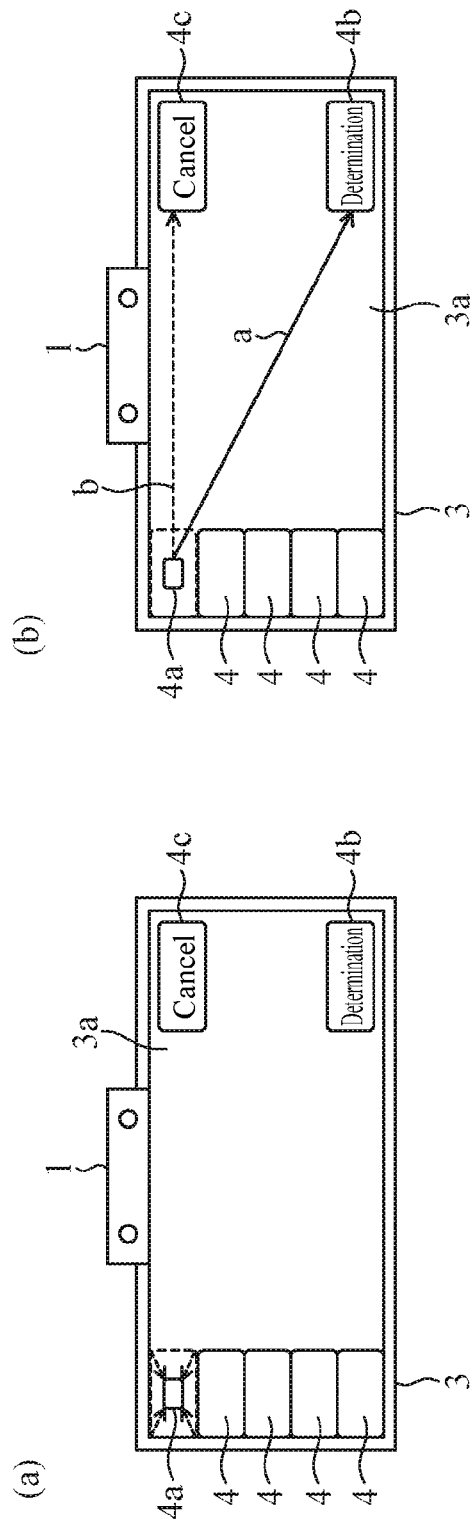
FIGS. 9(a) and 9(b) are diagrams each of which illustrates an example of a display screen for performing eye gaze guidance by arranging a gaze target object and a target object to be gazed at next at different positions.

FIG. 9 is a diagram illustrating an example of a display screen for performing eye gaze guidance by arranging a gaze target object and a target object to be gazed at next at different positions, and FIGS. 9(*a*) and 9(*b*) illustrate a case in which the display unit 3 is an IP display. In FIGS. 9(*a*) and 9(b), a plurality of selection keys serving as first gaze target objects is arranged on the left side of the display screen. On the other hand, the determination key 4b and the cancel key 4c that serve as second gaze target objects are arranged at the bottom right corner and the top right corner of the screen, respectively. Here, as described above, the selection key is a key representing a functional item, and the determination key is a key for determining the functional item selected using the selection key. In addition, the cancel key is a key for canceling the functional item selected using the selection key, and a key to cancel a key selected once for selecting another selection key.

Here, when the driver gazes at the top-left selection key 4a as the first gaze target object, the selection key 4a is displayed in such a manner as to be gradually scaled down, and calibration data for the selection key 4a is acquired in this state. This is executed by performing the following sequence. In the flowchart in FIG. 7, the driver is determined to be in the state of gazing at the top-left selection key 4a (step ST1), the selection key 4a is displayed to be scaled down in steps ST2 and ST3, display information of the selection key 4a serving as the gaze target object is output in step ST4, and a calibration control signal is output in step ST5.

Next, when the driver gazes at the determination key 4b as the second gaze target object, the determination key 4b is similarly displayed in such a manner as to be gradually scaled down, and calibration data for the determination key 4b is acquired in this state. Also in this case, the above-described flowchart in FIG. 7 is similarly executed. As a result, when the eye gaze of the driver moves as indicated by the solid line a in FIG. 9(b), calibration of eye gaze direction detection information can be executed at 2 points on the diagonal of the display unit 3. Alternatively, when the driver gazes at the cancel key 4c as the second gaze target object, the cancel key 4c is similarly displayed in such a manner as to be gradually scaled down, and calibration data for the cancel key 4c is acquired in this state. As a result, when the eye gaze of the driver moves as indicated by the broken line b in FIG. 9(b), calibration of eye gaze direction detection information can be executed at 2 points on one side of the display unit 3.

Note that, it is unknown which of the selection keys 4 the driver gazes at as the first gaze target object.

However, in the example illustrated in FIG. 9, when the bottom-left selection key 4 on the display screen is selected, if the determination key 4b is subsequently gazed at, calibration of eye gaze direction detection information can be executed at 2 points on one side of the display unit 3. Similarly, if the cancel key 4c is gazed at instead of the determination key 4b, calibration of eye gaze direction detection information can be executed at 2 points on the diagonal of the display unit 3.

Further, since it is considered that the driver is highly likely to subsequently gaze at the determination key 4b after gazing at a selection key, when the bottom-left selection key 4 on the display screen is selected, the displays of the determination key 4b and the cancel key 4c may be exchanged to each other. For improving the accuracy of calibration of eye gaze direction detection information, at first, it is desirable to acquire calibration data at 2 points on the diagonal of the display unit 3 rather than at 2 points on one side of the display unit 3. Thus, by changing the positions of the determination key, the cancel key, and the like according to the selection key at which the driver gazes, the accuracy of calibration of eye gaze direction detection information can be improved. In this case, in the flowchart in FIG. 7, after the bottom-left selection key 4a is displayed to be scaled-down, in steps ST2 and ST3, the arrangements of the determination key 4b and the cancel key 4c is exchanged to each other. This is executed by the display arrangement changeable unit 220 of the eye gaze guidance unit 22. Then, when it is determined that the driver gazes at the determination key that has moved to be displayed at the top right, in the flowchart in FIG. 7, the determination key that has moved to be displayed at the top right is displayed to be scaled-down, and calibration data is acquired.

In the present embodiment, by utilizing the fact that the determination key 4b is generally manipulated for finally determining the manipulation selected using the selection key 4a, when the gaze target object determined to be gazed at by the driver is a selection key (first gaze target object) 4a, the determination key (second gaze target object) 4b to be gazed at subsequently to the selection key is arranged at a position different from the position of the selection key 4a on the display screen 3a of the display unit 3.

As a result, when the driver gazes at the selection key 4a, a display size of the selection key 4a is scaled down, and the eye gaze is guided to the reference point. Then, the eye gaze is guided from this gaze state to the determination key 4b.

Specifically, the target object display changeable unit 221 of the eye gaze guidance unit 22 generates display change information for scaling down a gaze target object based on the gaze state of the gaze target object.

The display state management unit 222 outputs screen control information based on a current display state and the display change information. The screen control information is used for performing instruction so as to achieve a display mode in which the gaze target object is scaled down toward the reference point from the current display state. As a result, the gaze target object is gradually scaled down toward the reference point until the gaze target object becomes a predetermined size. Here, the predetermined size refers to a state in which the gaze target object is small enough for acquiring calibration data, and refers to, for example, a rectangle having one side of about 5 mm to 1 cm, or a circle having a diameter of such a size, or other shapes.

As described above, by arranging the selection key 4a and the determination key 4b at positions different from each other on the display screen 3a, the eye gaze of the driver is naturally guided from the selection key 4a to the determination key 4b.

Thus, calibration time can be shortened and calibration accuracy can be improved.

Here, the description has been given for the case in which the selection key 4a is used as a gaze target object, and the determination key 4b is used as a gaze target object to be gazed at subsequently to the selection key 4a. However, this embodiment is not limited to such a case.

For example, based on icon manipulation histories collected irrespective of manipulating persons, a selection ratio at which a corresponding icon is selected subsequently to an icon at which the driver has first gazed (first gaze target object) is obtained, and an icon having the selection ratio exceeding a threshold value may be used as the second gaze target object.

Figure 10:
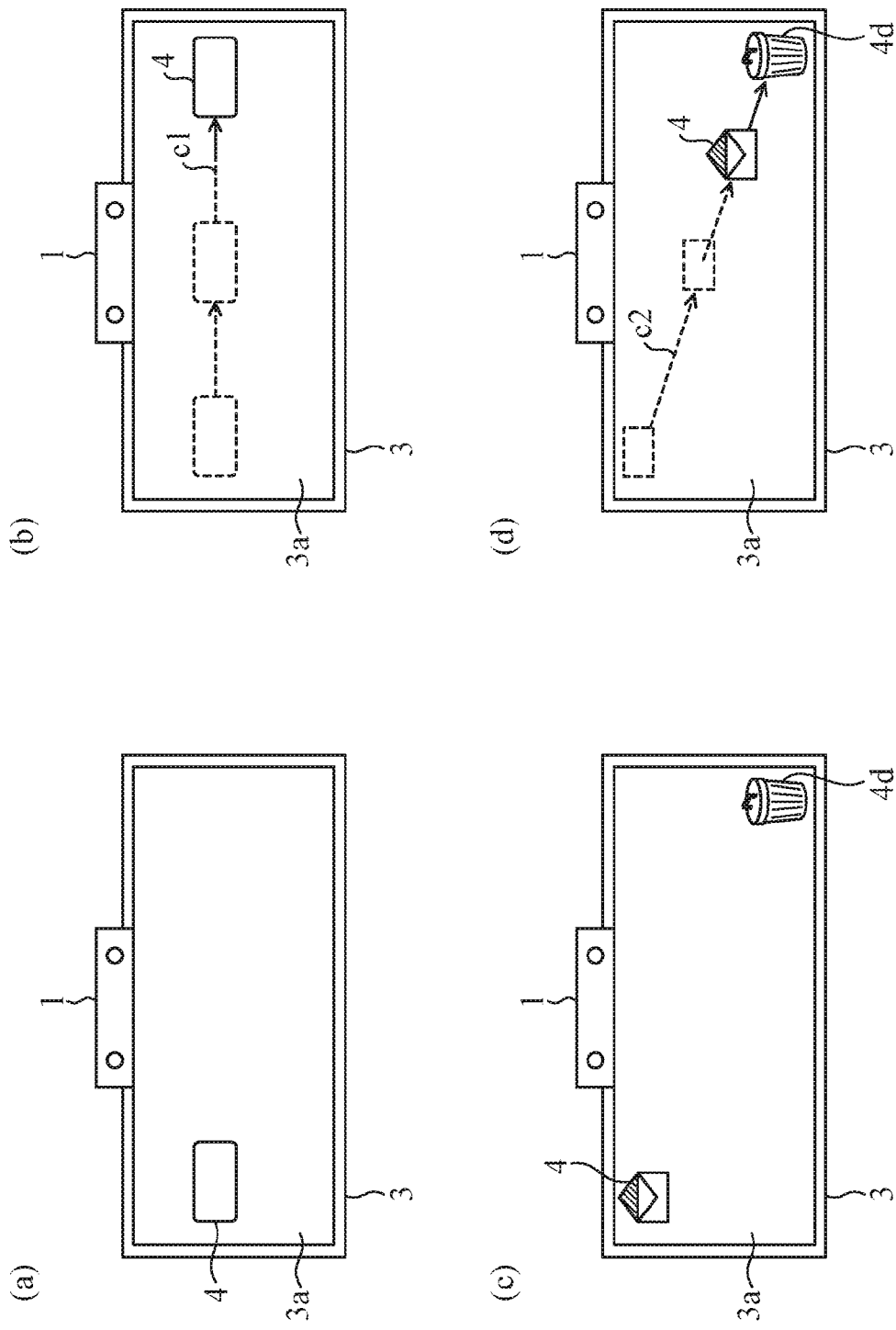
FIGS. 10(a) to 10(d) are diagrams each of which illustrates an example of a display screen for performing eye gaze guidance by moving a gaze target object.

FIG. 10 shows an example of a display screen for performing eye gaze guidance by moving a gaze target object, and FIGS. 10(a) to 10(d) illustrate a case in which the display unit 3 is an IP display.

In the present embodiment, when the driver is gazing at a gaze target object as illustrated in FIG. 10(a), the gaze target object 4 is moved in a predefined direction c1 as illustrated in FIG. 10(b).

Specifically, when it is determined based on eye gaze state information that the driver is gazing at a gaze target object, the target object display changeable unit 221 generates display change information for moving the gaze target object. The display change information represents a moving angle (the direction c1) and a moving speed at which the gaze target object is moved and the like. By obtaining current display information from the display state management unit 222, and outputting display change information to the display state management unit 222, the target object display changeable unit 221 moves the gaze target object 4 from, for example, the left side to the right side on the display screen 3a as illustrated in FIG. 10(b).

In this manner, through the display change of moving the gaze target object 4 at which the driver gazes, the eye gaze of the driver is guided in a predefined direction c1. Thus, the eye gaze is guided, so that calibration data can be acquired for the gaze target object before and after the movement. As a result, calibration accuracy is improved.

Namely, in the first embodiment, the gaze target object does not necessarily have to be scaled down. Note that, the gaze target object can be moved from the state in FIG. 10(a) to the state in FIG. 10(b) by executing the above-described flowchart in FIG. 7.

Further, as a gaze target object 4 to be moved, for example, an opened mail icon as illustrated in FIG. 10(c) can be considered. When an opened mail is deleted, the mail icon serving as the gaze target object 4 is moved in the direction c2 toward a trash icon 4d as illustrated in FIG. 10(d), as if the mail icon is thrown away into the trash icon.

Through the processing, the eye gaze of the driver is guided from the position where the driver gazed the mail icon at first, to the position of the trash icon 4d. At this time, by arranging the mail icon and the trash icon 4d on the diagonal, calibration data can be acquired similarly to the case of the selection key and the determination key.

Figure 11:
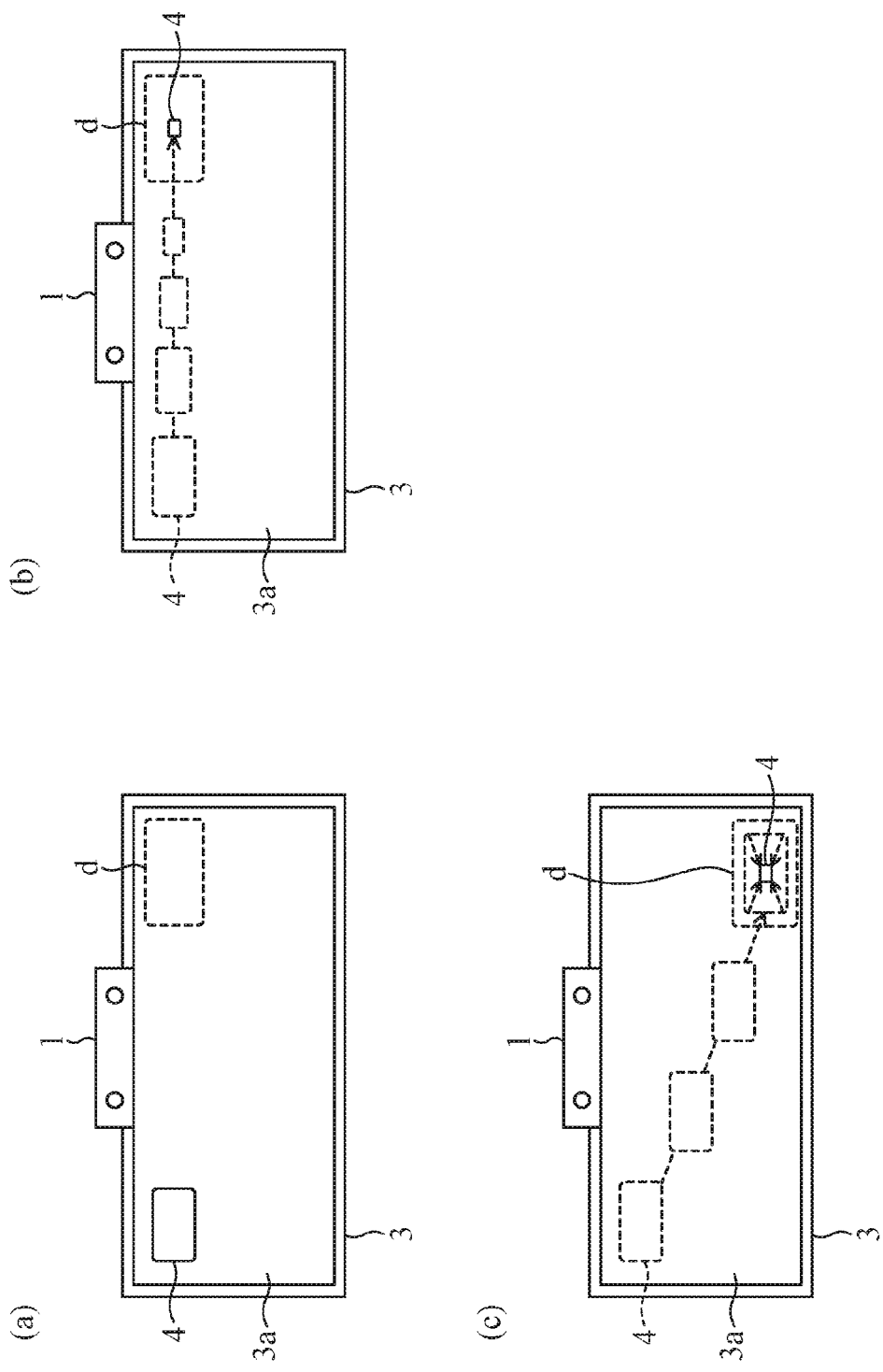
FIGS. 11(a) to 11(c) are diagrams each of which illustrates another example of a display screen for performing eye gaze guidance by moving a gaze target object.

FIG. 11 is a diagram illustrating another example of a display screen for performing eye gaze guidance by moving a gaze target object, and FIGS. 11(a) to 11(c) illustrate a case in which the display unit 3 is an IP display.

The display region d is the position where calibration accuracy of eye gaze direction detection information is the worst among positions (display regions) on the display screen 3a of the display unit 3. Here, the position where calibration accuracy is the worst can be considered to be a position where calibration has never been executed yet, or a position where the accuracy is the worst among positions where calibration has been executed in the past. In the present embodiment, the gaze target object is moved to the display region d where calibration accuracy is the worst, and brought into a scaled down state. In addition, as indicated by a broken line in FIG. 1 as an example, the position where calibration accuracy of eye gaze direction detection information is the worst in the past calibration is obtained from the eye gaze direction detection apparatus 1. For example, calibration accuracy information relating to calibration accuracy may be introduced to the eye gaze guidance unit 22. Note that, other broken line parts are not necessary here, and will be described later.

Specifically, based on the information on the position where calibration accuracy is the worst that is obtained from the eye gaze direction detection apparatus 1, and current display information obtained from the display state management unit 222, the target object display changeable unit 221 of the eye gaze guidance unit 22 generates display change information for moving the gaze target object 4 to the display region d. In addition, based on the current display information obtained from the display state management unit, the target object display changeable unit 221 generates display change information for gradually scaling down the gaze target object. The display change information for achieving both of them is given to the display state management unit 222. Based on the display change information, the display state management unit 222 generates screen control information for moving the gaze target object 4 to the display region d while scaling down the gaze target object 4. Through the processing, as illustrated in FIG. 11(b), the gaze target object 4 is moved to the display region d while being scaled down. By performing the above-described processing, calibration is executed in the display region d. The calibration accuracy in the display region d can be accordingly improved.

In addition, other than the case in which the gaze target object is moved while being scaled down to reach the display region d as illustrated in FIG. 11(b), as illustrated in FIG. 11(c), the gaze target object may be scaled down at the timing when the gaze target object reaches the display region d. Alternatively, the scaling-down display of the gaze target object is not necessarily required and may be omitted.

In addition, in the above description, an example is described in which the gaze target object is moved to the display region d including the position where calibration accuracy is the worst. However, the gaze target object does not necessarily have to be moved to a predefined reference point, and the gaze target object is only required to be moved basically to the display region d preferentially. This is because it can be considered that, for example, even though calibration accuracy is good, if there is a display region where calibration of eye gaze direction detection information has never been executed since key-on, the display region is first prioritized.

Figure 12:
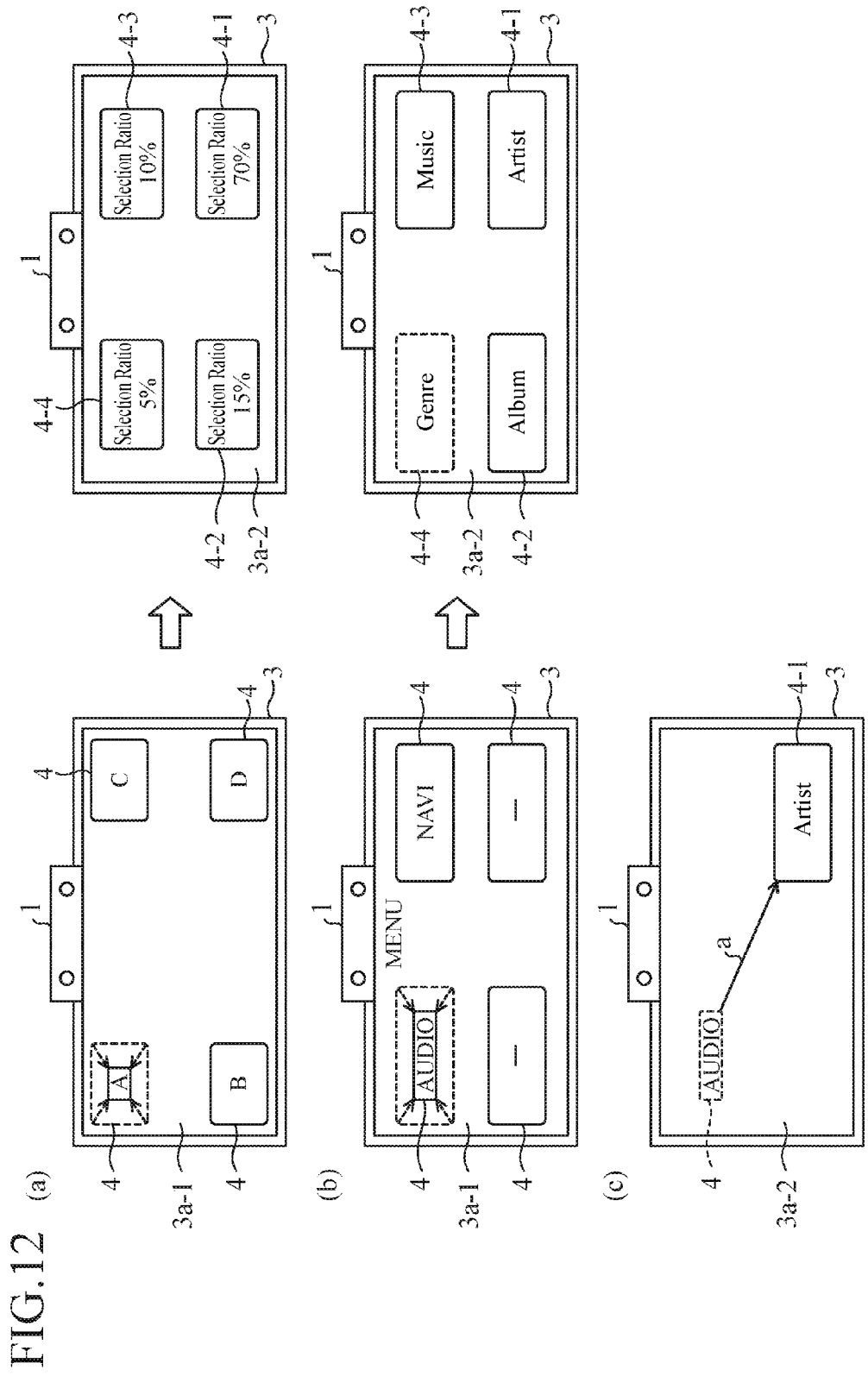
FIGS. 12(a) to 12(c) are diagrams each of which illustrates an example of a display screen for performing eye gaze guidance when a screen transitions.

FIG. 12 is a diagram illustrating an example of a display screen for performing eye gaze guidance when a screen transitions, and FIGS. 12(a) to 12(c) illustrate a case in which the display unit 3 is an IP display.

In FIG. 12(a), a scaled-down icon A at which the driver gazes (first gaze target object) is associated with an icon (second gaze target object) 4-1 to be gazed at subsequently to the icon A. For example, the above-described association is executed by obtaining, based on icon manipulation histories collected irrespective of manipulating persons, the selection ratio of each icon manipulation selected subsequently to the icon at which the driver has first gazed (first gaze target object), and using an icon corresponding to a manipulation having the selection ratio exceeding a threshold value as the second gaze target object. Here, the association based on icon manipulation histories can be easily conceived by the one skilled in the art so that the description is omitted here.

In the operation in FIG. 12, when it is determined that a gaze target object is the first gaze target object from the identification number of the gaze target object, the display arrangement changeable unit 220 of the eye gaze guidance unit 22 identifies the second gaze target object to be gazed at subsequently to the first gaze target object. Here, the second gaze target object to be gazed at subsequently to the first gaze target object is the gaze target object 4-1 having the highest selection ratio.

Next, the display arrangement changeable unit 220 generates screen arrangement change information for arranging the second gaze target object at a position diagonal to the first gaze target object in a display screen 3a-2, which is different from a display screen 3a-1 displaying the first gaze target object and displayed after transition from the display screen 3*a*-1, and outputs the generated screen arrangement change information.

Based on the screen arrangement change information, the display control unit 23 arranges the gaze target object 4-1 serving as the second gaze target object in the display screen 3*a*-2 at the position diagonal to the gaze target object A serving as the first gaze target object that was displayed on the display screen 3*a*-1.

In the present embodiment, a screen transitions from the display screen (first display screen) 3*a*-1 displaying the first gaze target object determined to be gazed at by the driver to the display screen (second display screen) 3*a*-2 displaying the second gaze target object. At this time, the first and second gaze target objects are respectively arranged on the display screens 3*a*-1 and 3*a*-2, at positions diagonal to each other.

For example, as illustrated in FIG. 12(*b*), when the "AUDIO" button on the display screen 3*a*-1 is manipulated, the "artist" button for selecting the artist of music that is highly likely to be manipulated subsequently to the "AUDIO" button is arranged at the diagonal position on the display screen 3*a*-2.

With this configuration, through the screen transition, the eye gaze of the driver is guided along a diagonal line as illustrated in FIG. 12(*c*), and moves by a distance a. As a result, calibration data required for calibration can be effectively acquired two-dimensionally, namely, vertically and horizontally, so that calibration accuracy can be promptly improved.

Note that, in the above, an example is described in which the second gaze target object is displayed at the diagonal position with respect to the first gaze target object. However, this embodiment is not limited to such a case. For example, in FIG. 12(*a*), when it is determined that the gaze target object A is gazed at, in subsequent screen transition, the gaze target object 4-1 may be displayed at any position such as top right, bottom left, the screen central part, or the like. Such non-mandatory display position may be set in consideration of various conditions like calibration accuracy, the status of a reference point where calibration has never been executed, and the like.

Further, in the above-described calibration processing, display for guiding the eye gaze of the driver in the display unit 3 is performed. If the display for guiding the eye gaze of the driver is constantly performed, the driver may feel uncomfortable.

Thus, if calibration accuracy of eye gaze direction detection information exceeds a predefined threshold value A, the accuracy of eye gaze direction detection information may be determined to be sufficient, and in such a case, the eye gaze guidance mode is canceled. Here, the predefined threshold value A is set to an appropriate value determined to enable manipulation without major troubles in manipulating the apparatus based on eye gaze direction detection information.

Figure 13:
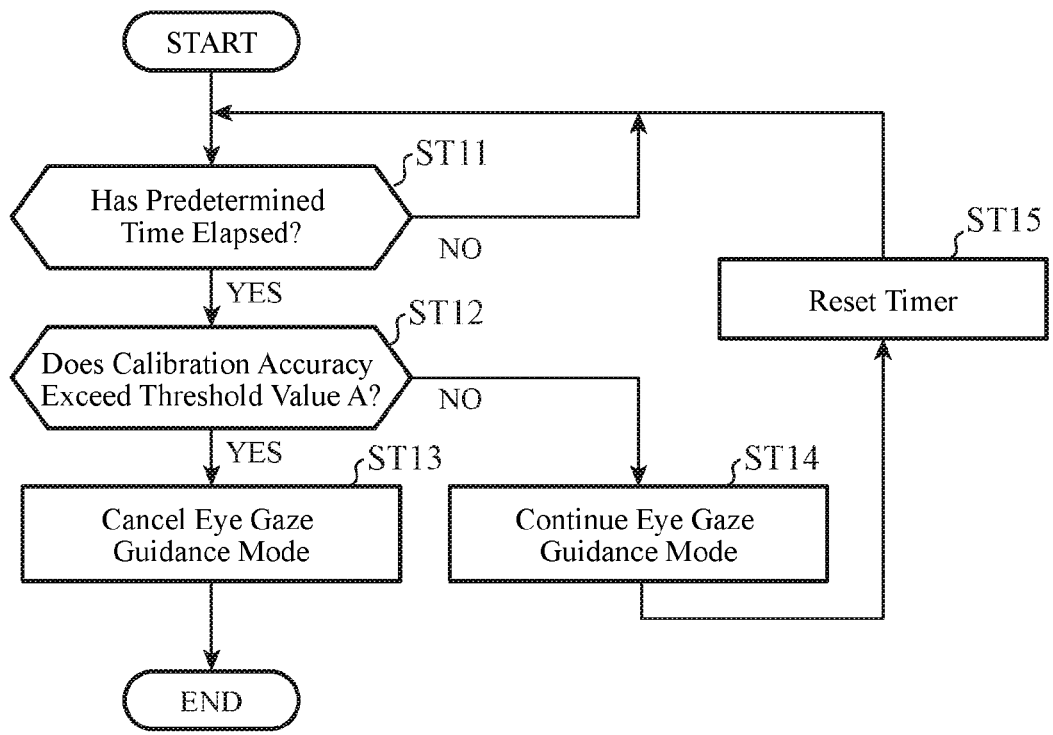
FIG. 13 is a flowchart illustrating cancel processing of an eye gaze guidance mode.

FIG. 13 is a flowchart illustrating cancel processing of the eye gaze guidance mode.

The flowchart in FIG. 13 is started triggered by a turning-on operation of a key switch, and executed without direct relation to the flowchart illustrated in FIG. 7. In the control idea shown in this flowchart, display for guiding the eye gaze of the driver is executed for a predetermined time (e.g., 5 to 10 minutes) from the key-on. Then, when it is determined that the accuracy of eye gaze direction detection information of the eye gaze direction detection apparatus 1 has accuracy sufficient for manipulating the target apparatus at a time point at which 5 to 10 minutes have passed, the display for guiding the eye gaze of the driver is ended. On the other hand, when the accuracy of eye gaze direction detection information of the eye gaze direction detection apparatus 1 does not have accuracy sufficient for manipulating the target apparatus, the display for guiding the eye gaze of the driver is further executed for about 5 to 10 minutes, and it is determined whether the above-described sufficient accuracy is satisfied. Due to such a processing, excessive execution of the display for guiding the eye gaze of the driver is suppressed.

The description will be given below in accordance with the flowchart in FIG. 13.

First, the calibration control unit 21 initially starts a timer triggered by key-on, and the timer determines whether a predetermined time (e.g., 10 minutes) has elapsed (step ST11). In this step, when the predetermined time has not elapsed (step ST11; NO), the determination in step ST11 is repeated.

When the predetermined time has elapsed (step ST11; YES), the calibration control unit 21 determines whether the calibration accuracy obtained in processing performed from the key-on until the predetermined time elapses exceeds a predefined threshold value A (step ST12). In the above, it is described that calibration accuracy information is given by the eye gaze direction detection apparatus 1 to the eye gaze guidance unit 22. Here, the information may also be given to the calibration control unit 21. This is indicated by a broken line in FIG. 1 for reference.

When it is determined that the calibration accuracy exceeds the threshold value A (step ST12; YES), the calibration control unit 21 instructs the eye gaze direction detection apparatus 1 to stop calibration processing, and notifies the eye gaze guidance unit 22 of this determination result.

Upon receiving this determination result, the eye gaze guidance unit 22 cancels the eye gaze guidance mode (step ST13). At this time, the eye gaze guidance unit 22 does not generate screen arrangement change information and display change information for eye gaze guidance, and the display unit 3 does not perform display for guiding the eye gaze of the driver.

On the other hand, when it is determined that the calibration accuracy is equal to or less than the threshold value A (step ST12; NO), the calibration control unit 21 continues calibration processing performed by the eye gaze direction detection apparatus 1. Namely, by initializing the timer in step ST 15 and returning the processing to step ST11, the display for guiding the eye gaze of the driver is further executed until the predetermined time elapses from this time point.

In addition, in the above first embodiment, a specific icon or the like has been described an example of a predefined gaze target object. However, the gaze target object does not necessarily have to be predefined.

Using any icon or the like at which the driver gazes as a gaze target object, the eye gaze guidance of the driver can be performed in a similar manner to the above.

As described above, according to the first embodiment, since the eye gaze of the driver is guided toward a predefined direction or position, by measuring calibration data before and after the guidance, calibration data can be obtained at a plurality of reference points. In addition, by guiding the eye gaze toward a predetermined direction or position, calibration data for a moving angle of the eye gaze can be obtained. With this configuration, calibration of eye gaze direction detection can be accurately and promptly performed.

In addition, according to the first embodiment, since the eye gaze guidance unit 22 scales down a gaze target object determined to be gazed at by the driver toward a reference point, the eye gaze of the driver is guided to the reference point of the gaze target object, so that measurement accuracy of each reference point can be improved. With this configuration, calibration accuracy can be improved.

Furthermore, according to the first embodiment, the eye gaze guidance unit 22 arranges the first gaze target object determined to be gazed at by the driver, and the second gaze target object to be gazed at subsequently to the first gaze target object, at different positions in the display unit 3. With this configuration, the eye gaze of the driver is guided from the first gaze target object to the second gaze target object, and calibration of eye gaze direction detection information can be accurately and promptly performed.

Furthermore, according to the first embodiment, the first and second gaze target objects are arranged at diagonal positions on the display screen 3a of the display unit 3. With this configuration, calibration data can be obtained two-dimensionally, namely, vertically and horizontally, and calibration of eye gaze direction detection information can be accurately and promptly performed.

Furthermore, according to the first embodiment, when the screen transitions from the first display screen on which a first gaze target object being gazed at is displayed to the second display screen, the second gaze target object is arranged at the position diagonal to the first gaze target object.

With this configuration, calibration of eye gaze direction detection information can be accurately and promptly performed as well.

Furthermore, according to the first embodiment, the eye gaze guidance unit 22 moves the gaze target object determined to be gazed at by the driver in a predefined direction on the display screen 3a of the display unit 3.

With this configuration, calibration can be executed for a moving angle of the eye gaze. Thus, calibration of eye gaze direction detection information can be accurately and promptly performed.

Furthermore, according to the first embodiment, a gaze target object is moved to a predefined position on the display screen 3a of the display unit 3. With this configuration, calibration of eye gaze direction detection information can be accurately and promptly performed.

Furthermore, according to the first embodiment, a gaze target object is moved preferentially to the position where the calibration accuracy of eye gaze direction detection is the worst, among predefined positions on the display screen 3a of the display unit 3. In addition, desirably, the gaze target object is further brought into a scaled-down state. With this configuration, since calibration is executed at the corresponding position, calibration accuracy at the corresponding position can be promptly improved.

Furthermore, according to the first embodiment, the calibration control unit 21 controls calibration according to a predefined condition. With this configuration, calibration start and end can be performed at appropriate timings.

In particular, when this condition is a driver's switch manipulation, calibration can be performed at a timing intended by the driver.

In addition, when the lapse of time from when the driver has gazed at a gaze target object is used as the above-described timing, calibration measurement can be performed without making the driver be aware. For example, this is suitable for the case of performing calibration while the driver is driving the vehicle.

Furthermore, according to the first embodiment, the eye gaze guidance unit 22 cancels eye gaze guidance when the calibration accuracy of eye gaze direction detection information is sufficiently-high exceeding a predefined threshold value. With this configuration, constant execution of the display for guiding the eye gaze of the driver can be suppressed, and the driver can be prevented from feeling uncomfortable.

Second Embodiment

Figure 14:
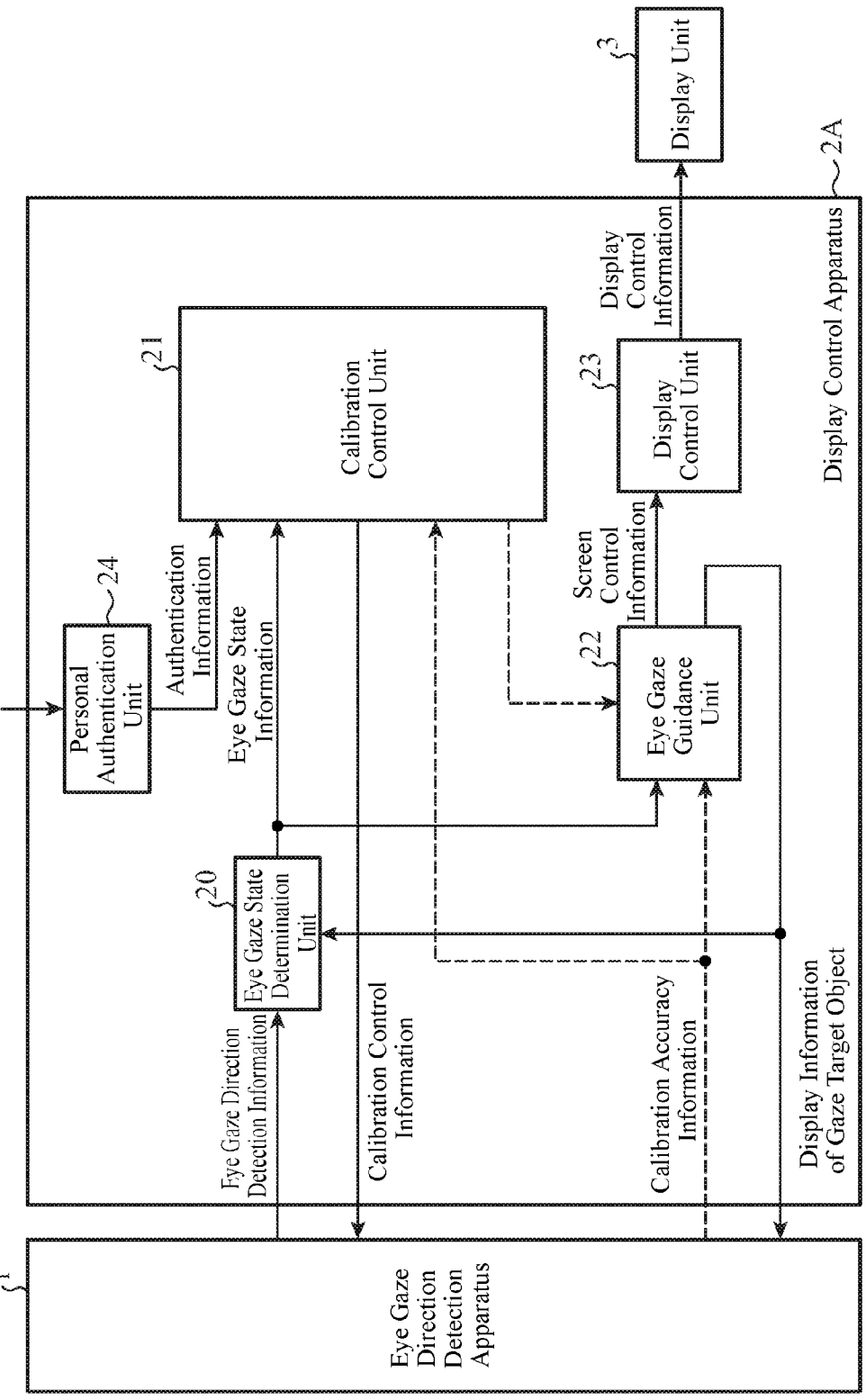
FIG. 14 is a block diagram illustrating a configuration of an eye gaze direction detection system according to a second embodiment of the present invention.

FIG. 14 is a block diagram illustrating a configuration of an eye gaze direction detection system according to a second embodiment of the present invention. Eye gaze direction detection information detected by an eye gaze direction detection unit 12 includes a detection error resulting from individual differences of drivers. Thus, for ensuring detection accuracy of eye gaze direction detection information, it is desirable to execute calibration for each driver.

Similarly to the first embodiment, the eye gaze direction detection system illustrated in FIG. 14 is a system mounted on a movable body such as a vehicle to detect the eye gaze direction of a driver, and includes an eye gaze direction detection apparatus 1, a display control apparatus 2A, and a display unit 3. Here, in FIG. 14, to the configurations similar to those in FIG. 1, the same reference numerals with FIG. 1 are assigned, and the description thereof will be omitted.

In addition to the configurations in the first embodiment, the display control apparatus 2A according to the second embodiment includes a personal authentication unit 24. The personal authentication unit 24 authenticates a driver based on authentication information of each driver. For example, examples of the authentication information include photograph information obtained by photographing the face of a driver, biological information of the driver, device information of a mobile terminal owned by the driver, and the like.

By checking these pieces of information with registration information of each individual driver, the personal authentication unit 24 authenticates the driver to verify whether the driver is a preregistered driver. The authentication result obtained by the personal authentication unit 24 is output to a calibration control unit 21.

The calibration control unit 21 instructs the eye gaze direction detection apparatus 1 to perform calibration for the driver authenticated by the personal authentication unit 24.

For example, the calibration control unit 21 makes a calibration unit 13 calculate calibration data of eye gaze direction detection information for the driver authenticated by the personal authentication unit 24. Thus, calibration data is stored in a memory 14 in association with each individual.

In addition, the calibration control unit 21 makes the eye gaze direction detection unit 12 correct calculation processing of detecting an eye gaze direction, using calibration data corresponding to the driver authenticated by the personal authentication unit 24, among calibration data stored in the memory 14.

With this configuration, calibration of eye gaze direction detection information can be executed for each driver authenticated by the personal authentication unit 24.

Similarly to the above-described first embodiment, each of the eye gaze state determination unit 20, the calibration control unit 21, the eye gaze guidance unit 22, the display control unit 23, and the personal authentication unit 24 can be implemented as a specific means in which hardware and software cooperate with each other, by a microcomputer executing a program in which processing specific to the second embodiment is described, for example.

As described above, according to the second embodiment, the display control apparatus 2A further includes the personal authentication unit 24 to authenticate a subject. With this configuration, the calibration control unit 21 can execute calibration of eye gaze direction detection information output by the eye gaze direction detection apparatus 1 for each subject, using calibration data of each subject authenticated by the personal authentication unit 24.

In addition, in the present invention, the embodiments can be freely combined to each other, any constituent element in the embodiments can be modified, or any constituent element in the embodiments can be omitted, without departing from the scope of the invention.

INDUSTRIAL APPLICABILITY

The display control apparatus according to the present invention can accurately and promptly perform calibration of eye gaze direction detection information of a subject. Thus, for example, the display control apparatus is suitable for a driving assistance system to assist driving using an eye gaze direction of a driver.

REFERENCE SIGNS LIST 1 eye gaze direction detection apparatus
2, 2A calibration control apparatus
3 display unit
3a, 3a-1, 3a-2, 3b display screen
4, 4b, 4c, 4d, 4-1 to 4-4 gaze target object
4a scaled-down gaze target object
5 switch
10 infrared LED
11 eye gaze detection camera
12 eye gaze direction detection unit
13 calibration unit
14 memory
20 eye gaze state determination unit
21 calibration control unit
22 eye gaze guidance unit
23 display control unit
24 personal authentication unit
200 target object determination unit
201 gaze state determination unit
210 control determination unit
211 control command output unit
220 display arrangement changeable unit
221 target object display changeable unit
230 display state management unit
231 display output unit

The invention claimed is:

1. A display control apparatus to use a display object displayed by a display unit as a gaze target object, and to control calibration of an eye gaze direction detection apparatus based on the gaze target object, the display control apparatus comprising:
an eye gaze state determinator to determine, based on eye gaze direction detection information detected by the eye gaze direction detection apparatus and display information of the gaze target object, whether a subject is gazing at the gaze target object existing in an eye gaze direction of the subject;
an eye gaze guider to output display information of the gaze target object and screen control information relating to a display mode of the gaze target object, and to guide an eye gaze of the subject by changing the display mode of the gaze target object when the subject is determined to be gazing at the gaze target object;
a display controller to output display control information for controlling the display unit, based on the screen control information output by the eye gaze guider; and
a calibration controller to output a calibration control signal toward the eye gaze direction detection apparatus when the subject is determined to be gazing at the gaze target object,
wherein the gaze target object is an icon or a button displayed by an intelligent panel functioning as the display unit, or by the display unit of a car navigation apparatus, or a marking displayed by a head-up display as the display unit.

2. The display control apparatus according to claim 1, wherein the eye gaze guider scales down the gaze target object determined to be gazed at by the subject, toward a reference point.

3. The display control apparatus according to claim 1, wherein the eye gaze guider arranges a first gaze target object determined to be gazed at by the subject, and a second gaze target object to be gazed at subsequently to the first gaze target object, at different positions on the display unit.

4. The display control apparatus according to claim 3, wherein the second gaze target object is a determination key to determine a manipulation being selected by using the first gaze target object.

5. The display control apparatus according to claim 3, wherein the eye gaze guider arranges the first and the second gaze target objects at diagonal positions on a display screen of the display unit.

6. The display control apparatus according to claim 3, wherein, when a screen transitions from a first display screen displaying the first gaze target object to a second display screen displaying the second gaze target object, the eye gaze guider respectively arranges the first and the second gaze target objects on the first and the second display screens, at positions diagonal to each other.

7. The display control apparatus according to claim 1, wherein the eye gaze guider moves the gaze target object determined to be gazed at by the subject, in a predefined direction on a display screen of the display unit.

8. The display control apparatus according to claim 1, wherein the eye gaze guider moves the gaze target object to a predefined position on a display screen of the display unit.

9. The display control apparatus according to claim 8, wherein the eye gaze guider moves the gaze target object preferentially to a reference point where calibration accuracy of eye gaze direction detection information is worst, among a plurality of reference points predefined on a display screen of the display unit, and brings the gaze target object into a scale-down state.

10. The display control apparatus according to claim 1, further comprising a personal authenticator to authenticate a subject,
wherein the calibration controller outputs a calibration control signal together with personal recognition information of a subject authenticated by the personal authenticator.

11. The display control apparatus according to claim 1, wherein the calibration controller outputs the calibration control signal in accordance with a predefined condition.

12. The display control apparatus according to claim 11, wherein, when a switch manipulation performed by a subject is received, the calibration controller outputs, as a calibration control signal, at least a calibration data save start command or a save stop command.

13. The display control apparatus according to claim 11, wherein, when the eye gaze state determinator determines that the subject is gazing at the gaze target object, the calibration controller outputs, as a calibration control signal, at least a calibration data save start command.

14. The display control apparatus according to claim 11, wherein, when a gaze state of the subject has passed a predefined time, the calibration controller outputs, as a calibration control signal, at least a calibration data save stop command.

15. The display control apparatus according to claim 1, wherein the eye gaze guider cancels the eye gaze guidance when calibration accuracy of the eye gaze direction detection apparatus exceeds a predefined threshold value.

16. A control method of a display control apparatus to use a display object displayed by a display unit, as a gaze target object, and to control calibration of an eye gaze direction detection apparatus based on the gaze target object, the control method comprising:
- determining, in a gaze state determinator, based on eye gaze direction detection information detected by the eye gaze direction detection apparatus and display information of the gaze target object, whether a subject is gazing at the gaze target object existing in an eye gaze direction of the subject;
- outputting, in an eye gaze guider, display information of the gaze target object and screen control information relating to a display mode of the gaze target object, and guiding an eye gaze of the subject by changing the display mode of the gaze target object when the subject is determined to be gazing at the gaze target object;
- outputting, in a display controller, display control information for controlling the display unit, based on the screen control information output by the eye gaze guider; and
- outputting, in a calibration controller, a calibration control signal toward the eye gaze direction detection apparatus when the subject is determined to be gazing at the gaze target object,
- wherein the gaze target object is an icon or a button displayed by an intelligent panel functioning as the display unit, or by the display unit of a car navigation apparatus, or a marking displayed by a head-up display as the display unit.

17. An eye gaze direction detection system including an eye gaze direction detection apparatus to detect an eye gaze direction of a subject, a display control apparatus to use a display object displayed by a display unit, as a gaze target object, and to control calibration of the eye gaze direction detection apparatus based on the gaze target object, and a display unit to perform display based on display control information from the display control apparatus,
wherein the display control apparatus is a display control apparatus to use a display object displayed by the display unit, as a gaze target object, and to control calibration of the eye gaze direction detection apparatus based on the gaze target object, and includes:
- an eye gaze state determinator to determine, based on eye gaze direction detection information detected by the eye gaze direction detection apparatus and display information of the gaze target object, whether a subject is gazing at the gaze target object existing in an eye gaze direction of the subject;
- an eye gaze guider to output display information of the gaze target object and screen control information relating to a display mode of the gaze target object, and to guide an eye gaze of the subject by changing the display mode of the gaze target object when the subject is determined to be gazing at the gaze target object;
- a display controller to output display control information for controlling the display unit, based on the screen control information output by the eye gaze guider; and
- a calibration controller to output a calibration control signal toward the eye gaze direction detection apparatus when the subject is determined to be gazing at the gaze target object,
wherein the gaze target object is an icon or a button displayed by an intelligent panel functioning as the display unit, or by the display unit of a car navigation apparatus, or a marking displayed by a head-up display as the display unit, and
wherein the eye gaze direction detection apparatus includes:
- an eye gaze direction detector to detect eye gaze direction detection information of the subject;
- a calibrator to calculate calibration data according to a calibration control signal output by the display control apparatus, based on eye gaze detection direction information detected by the eye gaze direction detector and display information of the gaze target object obtained from the display control apparatus; and
- a storage unit to store the calibration data.

18. The eye gaze direction detection system according to claim 17, wherein the calibrator of the eye gaze direction detection apparatus outputs the calibration control signal together with personal recognition information of a subject.

* * * * *